US010034921B2

(12) United States Patent
Chen et al.

(10) Patent No.: US 10,034,921 B2
(45) Date of Patent: Jul. 31, 2018

(54) PROTEINS WITH MODIFIED GLYCOSYLATION AND METHODS OF PRODUCTION THEREOF

(71) Applicant: Laboratoire Français du Fractionnement et des Biotechnologies, Les Ulis (FR)

(72) Inventors: Li-How Chen, Acton, MA (US); Harry M. Meade, Newton, MA (US)

(73) Assignee: Laboratoire Français du Fractionnement et des Biotechnologies, Les Ulis (FR)

( * ) Notice: Subject to any disclaimer, the term of this patent is extended or adjusted under 35 U.S.C. 154(b) by 0 days.

(21) Appl. No.: 14/767,100

(22) PCT Filed: Feb. 13, 2014

(86) PCT No.: PCT/IB2014/001236
§ 371 (c)(1),
(2) Date: Aug. 11, 2015

(87) PCT Pub. No.: WO2014/140927
PCT Pub. Date: Sep. 18, 2014

(65) Prior Publication Data
US 2015/0374801 A1 Dec. 31, 2015

Related U.S. Application Data

(60) Provisional application No. 61/764,502, filed on Feb. 13, 2013.

(51) Int. Cl.
| | | |
|---|---|---|
| *G01N 33/00* | (2006.01) | |
| *A01K 67/033* | (2006.01) | |
| *A61K 38/45* | (2006.01) | |
| *A01K 67/027* | (2006.01) | |
| *C12N 9/10* | (2006.01) | |
| *C07K 14/81* | (2006.01) | |

(52) U.S. Cl.
CPC .......... *A61K 38/45* (2013.01); *A01K 67/0275* (2013.01); *C07K 14/8125* (2013.01); *C12N 9/1081* (2013.01); *A01K 2207/05* (2013.01); *A01K 2217/15* (2013.01); *A01K 2217/206* (2013.01); *A01K 2267/01* (2013.01); *C12Y 204/99* (2013.01)

(58) Field of Classification Search
CPC .............................. A61K 38/45; A01K 67/0275
See application file for complete search history.

(56) References Cited

U.S. PATENT DOCUMENTS

| | | | |
|---|---|---|---|
| 4,399,216 A | 8/1983 | Axel et al. | |
| 4,517,294 A | 5/1985 | Bock et al. | |
| 4,632,981 A | 12/1986 | Bock et al. | |
| 4,816,397 A | 3/1989 | Boss et al. | |
| 4,816,567 A | 3/1989 | Cabilly et al. | |
| 4,873,316 A | 10/1989 | Meade et al. | |
| 4,946,778 A | 8/1990 | Ladner et al. | |
| 5,202,238 A | 4/1993 | Fell et al. | |
| 5,304,489 A | 4/1994 | Rosen | |
| 5,322,775 A * | 6/1994 | Clark ................. | A01K 67/0275 435/317.1 |
| 5,366,894 A | 11/1994 | Clark et al. | |
| 5,416,017 A | 5/1995 | Burton | |
| 5,476,995 A | 12/1995 | Clark et al. | |
| 5,545,806 A | 8/1996 | Lonberg et al. | |
| 5,545,807 A | 8/1996 | Surani et al. | |
| 5,576,040 A | 11/1996 | Moller et al. | |
| 5,589,604 A | 12/1996 | Drohan et al. | |
| 5,591,669 A | 1/1997 | Krimpenfort et al. | |
| 5,633,076 A * | 5/1997 | DeBoer .............. | A01K 67/0275 800/25 |
| 5,639,940 A | 6/1997 | Garner et al. | |
| 5,648,243 A | 7/1997 | Hurwitz et al. | |
| 5,648,253 A | 7/1997 | Wei | |
| 5,741,957 A | 4/1998 | Deboer et al. | |
| 5,750,172 A | 5/1998 | Meade et al. | |
| 5,756,687 A | 5/1998 | Denman et al. | |
| 5,780,009 A | 7/1998 | Karatzas et al. | |
| 5,827,690 A | 10/1998 | Meade et al. | |
| 5,831,141 A * | 11/1998 | Lubon ................ | A01K 67/0278 435/320.1 |
| 5,843,705 A | 12/1998 | DiTullio et al. | |
| 5,849,992 A | 12/1998 | Meade et al. | |
| 5,892,070 A | 4/1999 | Prieto et al. | |
| 5,945,577 A | 8/1999 | Stice et al. | |

(Continued)

FOREIGN PATENT DOCUMENTS

| | | |
|---|---|---|
| CN | 1273602 A | 11/2000 |
| CN | 1387399 A | 12/2002 |
| CN | 1607960 A | 4/2005 |
| CN | 1751739 A | 3/2006 |
| CN | 1944645 A | 4/2007 |
| CN | 101460522 A | 6/2009 |
| CN | 101495133 A | 7/2009 |
| CN | 101588817 A | 11/2009 |
| CN | 101802210 A | 8/2010 |
| CN | 101934071 A | 1/2011 |
| CN | 102660581 A | 9/2012 |
| DE | 40 00 939 A1 | 7/1991 |
| EP | 0 090 505 A2 | 10/1983 |
| EP | 0 114 589 A1 | 8/1984 |
| EP | 0 264 166 A1 | 4/1988 |
| EP | 0 279 582 A2 | 8/1988 |
| EP | 0475354 A2 | 3/1992 |

(Continued)

OTHER PUBLICATIONS

Dalziel, 2001, Glycobiology, 11:407-412.*

(Continued)

*Primary Examiner* — Valarie E Bertoglio
(74) *Attorney, Agent, or Firm* — Wolf, Greenfield & Sacks, P.C.

(57) ABSTRACT

In one aspect, the disclosure provides proteins with modified glycosylation and methods of their production. In aspect, the disclosure provides transgenic animals and cells for the production of proteins with modified glycosylation. In some embodiment, the modified glycosylation is increased sialylation.

14 Claims, 7 Drawing Sheets

(56) References Cited

U.S. PATENT DOCUMENTS

| | | |
|---|---|---|
| 5,965,789 A | 10/1999 | Lubon et al. |
| 6,013,857 A | 1/2000 | Deboer et al. |
| 6,063,905 A | 5/2000 | Capra et al. |
| 6,140,552 A | 10/2000 | Deboer et al. |
| 6,150,584 A | 11/2000 | Kucherlapati et al. |
| 6,194,553 B1 | 2/2001 | Lee et al. |
| 6,201,167 B1 | 3/2001 | Pothier |
| 6,204,431 B1* | 3/2001 | Prieto ............... A01K 67/0275 800/14 |
| 6,210,736 B1 | 4/2001 | Echelard et al. |
| 6,217,866 B1 | 4/2001 | Schlessinger et al. |
| 6,268,487 B1 | 7/2001 | Kutzko et al. |
| 6,271,436 B1 | 8/2001 | Piedrahita et al. |
| 6,441,145 B1 | 8/2002 | DiTullio et al. |
| 6,448,469 B1 | 9/2002 | Smith |
| 6,472,584 B1 | 10/2002 | Smith |
| 6,528,699 B1 | 3/2003 | Meade et al. |
| 6,545,198 B1 | 4/2003 | Echelard et al. |
| 6,548,653 B1 | 4/2003 | Young et al. |
| 6,580,017 B1 | 6/2003 | Echelard et al. |
| 6,593,463 B1 | 7/2003 | Chen et al. |
| 6,727,405 B1 | 4/2004 | Gordon et al. |
| 6,743,966 B2 | 6/2004 | Smith |
| 6,924,412 B1 | 8/2005 | de Groot et al. |
| 6,933,368 B2 | 8/2005 | Co et al. |
| 7,019,193 B2 | 3/2006 | DiTuillio et al. |
| 7,045,676 B1 | 5/2006 | Gordon et al. |
| 7,053,202 B2 | 5/2006 | O'Keefe et al. |
| 7,087,719 B2 | 8/2006 | Visuri et al. |
| 7,101,971 B2 | 9/2006 | Meade et al. |
| 7,354,594 B2 | 4/2008 | Chen et al. |
| 7,501,553 B2 | 3/2009 | Chen et al. |
| 7,531,632 B2 | 5/2009 | Perreault |
| 7,550,263 B2 | 6/2009 | Meade et al. |
| 7,632,980 B1 | 12/2009 | Chen et al. |
| 7,651,686 B2 | 1/2010 | Chen et al. |
| 7,700,321 B2 | 4/2010 | McPherson et al. |
| 7,867,491 B2 | 1/2011 | Yang et al. |
| 7,928,064 B2 | 4/2011 | DiTullio et al. |
| 7,939,317 B1 | 5/2011 | Gordon et al. |
| 8,173,860 B2 | 5/2012 | Meade et al. |
| 9,511,087 B2 | 12/2016 | Friedling et al. |
| 2002/0131957 A1 | 9/2002 | Gavin et al. |
| 2002/0144299 A1 | 10/2002 | Chen et al. |
| 2002/0155998 A1 | 10/2002 | Young et al. |
| 2003/0005468 A1 | 1/2003 | Meade et al. |
| 2003/0033618 A1 | 2/2003 | Smith |
| 2003/0036637 A1 | 2/2003 | Fulton |
| 2003/0046716 A1 | 3/2003 | Echelard et al. |
| 2003/0096974 A1 | 5/2003 | Ditullio et al. |
| 2003/0140358 A1 | 7/2003 | Nuijens et al. |
| 2003/0175884 A1 | 9/2003 | Umana et al. |
| 2003/0177513 A1 | 9/2003 | Echelard et al. |
| 2003/0204860 A1 | 10/2003 | Melican et al. |
| 2003/0213003 A1 | 11/2003 | Meade et al. |
| 2004/0006776 A1 | 1/2004 | Meade et al. |
| 2004/0025193 A1 | 2/2004 | Echelard et al. |
| 2004/0033561 A1 | 2/2004 | O'Keefe et al. |
| 2004/0068760 A1 | 4/2004 | Robl et al. |
| 2004/0092719 A1 | 5/2004 | Birck-Wilson et al. |
| 2004/0097710 A1 | 5/2004 | Visuri et al. |
| 2004/0098755 A1 | 5/2004 | Mulroy et al. |
| 2004/0102380 A1 | 5/2004 | Fulton et al. |
| 2004/0109847 A1 | 6/2004 | Chen et al. |
| 2004/0117863 A1 | 6/2004 | Edge et al. |
| 2004/0121303 A1 | 6/2004 | Gavin et al. |
| 2004/0132101 A1 | 7/2004 | Lazar et al. |
| 2004/0133931 A1 | 7/2004 | Gavin et al. |
| 2004/0143857 A1 | 7/2004 | Young et al. |
| 2004/0148648 A1 | 7/2004 | Behboodi et al. |
| 2004/0167320 A1 | 8/2004 | Couto et al. |
| 2004/0192595 A1 | 9/2004 | Murakami et al. |
| 2004/0205832 A1 | 10/2004 | Meade et al. |
| 2004/0226052 A1 | 11/2004 | Meade et al. |
| 2004/0226053 A1 | 11/2004 | Meade et al. |
| 2005/0013811 A1 | 1/2005 | Chen et al. |
| 2005/0037000 A1 | 2/2005 | Stavenhagen et al. |
| 2005/0060766 A1 | 3/2005 | Chen |
| 2005/0071890 A1 | 3/2005 | Chen et al. |
| 2005/0097625 A1 | 5/2005 | Meade et al. |
| 2005/0158832 A1 | 7/2005 | Young et al. |
| 2005/0160483 A1 | 7/2005 | Meade et al. |
| 2005/0169908 A1 | 8/2005 | Murakami et al. |
| 2005/0177882 A1 | 8/2005 | Gavin et al. |
| 2005/0181482 A1 | 8/2005 | Meade et al. |
| 2005/0186608 A1 | 8/2005 | Olsen |
| 2005/0192226 A1 | 9/2005 | Enkhbaatar et al. |
| 2005/0193431 A1 | 9/2005 | Echelard et al. |
| 2005/0197496 A1 | 9/2005 | Perreault |
| 2005/0208000 A1 | 9/2005 | Bernstein et al. |
| 2005/0229261 A1 | 10/2005 | Cheng et al. |
| 2005/0235371 A1 | 10/2005 | Chen et al. |
| 2005/0245444 A1 | 11/2005 | Echelard et al. |
| 2005/0260672 A1 | 11/2005 | Couto et al. |
| 2006/0026695 A1 | 2/2006 | Edge et al. |
| 2006/0057638 A1 | 3/2006 | Bosques et al. |
| 2006/0084598 A1 | 4/2006 | Blanco |
| 2006/0105347 A1 | 5/2006 | Meade et al. |
| 2006/0121004 A1 | 6/2006 | Echelard et al. |
| 2006/0123500 A1 | 6/2006 | Echelard et al. |
| 2006/0127950 A1 | 6/2006 | Bosques et al. |
| 2006/0130159 A1 | 6/2006 | Masiello et al. |
| 2006/0168671 A1 | 7/2006 | Gavin et al. |
| 2006/0174359 A1 | 8/2006 | Melican et al. |
| 2006/0178309 A1 | 8/2006 | Visuri et al. |
| 2006/0179493 A1 | 8/2006 | Meade et al. |
| 2006/0179500 A1 | 8/2006 | Meade et al. |
| 2006/0182744 A1 | 8/2006 | Strome et al. |
| 2006/0191025 A1 | 8/2006 | Echelard et al. |
| 2006/0191029 A1 | 8/2006 | Gavin et al. |
| 2006/0253913 A1 | 11/2006 | Huang et al. |
| 2006/0286548 A1 | 12/2006 | Liposky et al. |
| 2007/0015239 A1 | 1/2007 | Bihoreau et al. |
| 2007/0037192 A1 | 2/2007 | Ziomek et al. |
| 2007/0048300 A1 | 3/2007 | Taylor et al. |
| 2007/0092521 A1 | 4/2007 | McPherson et al. |
| 2007/0192878 A1 | 8/2007 | Perreault |
| 2008/0004212 A1 | 1/2008 | Echelard et al. |
| 2008/0019905 A9 | 1/2008 | Strome et al. |
| 2008/0063780 A1 | 3/2008 | Meade et al. |
| 2008/0118501 A1 | 5/2008 | Schindler et al. |
| 2008/0176786 A1 | 7/2008 | Ditullio et al. |
| 2009/0068193 A1 | 3/2009 | Chen et al. |
| 2009/0178147 A1 | 7/2009 | Harvey |
| 2009/0239788 A1 | 9/2009 | Chtourou et al. |
| 2009/0246194 A1 | 10/2009 | Meade et al. |
| 2010/0021612 A1 | 1/2010 | Meade et al. |
| 2010/0056757 A1 | 3/2010 | Perreault |
| 2010/0081794 A1 | 4/2010 | Liu et al. |
| 2010/0173323 A1 | 7/2010 | Strome et al. |
| 2011/0070167 A1 | 3/2011 | Enkhbaatar et al. |
| 2011/0082083 A1 | 4/2011 | Magneson et al. |
| 2011/0229460 A1 | 9/2011 | Meade |
| 2012/0058047 A9 | 3/2012 | Strome et al. |
| 2013/0149301 A1 | 6/2013 | Meade |
| 2013/0324619 A1 | 12/2013 | Chtourou |
| 2014/0046033 A1 | 2/2014 | Schindler et al. |
| 2014/0194360 A1 | 7/2014 | Frieling et al. |
| 2014/0206617 A1 | 7/2014 | Frieling et al. |
| 2014/0228301 A1 | 8/2014 | Meade et al. |
| 2014/0242182 A1 | 8/2014 | Evans et al. |
| 2014/0296490 A1 | 10/2014 | Faid et al. |
| 2015/0175678 A1 | 6/2015 | Cavacini et al. |
| 2015/0368334 A1 | 12/2015 | Meade et al. |
| 2015/0368357 A1 | 12/2015 | Meade et al. |
| 2015/0374801 A1 | 12/2015 | Chen et al. |
| 2016/0002330 A1 | 1/2016 | Meade |
| 2016/0039913 A1 | 2/2016 | Meade et al. |
| 2016/0089422 A1 | 3/2016 | Chtourou et al. |
| 2016/0129115 A1 | 5/2016 | Magneson et al. |
| 2016/0158676 A1 | 6/2016 | Hawkins et al. |
| 2016/0168229 A1 | 6/2016 | Paolantonacci et al. |
| 2016/0326547 A1 | 11/2016 | Meade et al. |

(56) References Cited

U.S. PATENT DOCUMENTS

| | | | |
|---|---|---|---|
| 2017/0121402 A1 | 5/2017 | Chtourou |
| 2017/0129966 A1 | 5/2017 | Masiello |
| 2017/0190753 A1 | 7/2017 | Abache |

FOREIGN PATENT DOCUMENTS

| | | |
|---|---|---|
| EP | 0 512 090 B1 | 1/1997 |
| EP | 0 791 652 A1 | 8/1997 |
| EP | 1 400 171 A1 | 3/2004 |
| EP | 1 945 665 B1 | 7/2008 |
| EP | 2 292 273 A2 | 3/2011 |
| FR | 2 861 080 A1 | 4/2005 |
| JP | 9-506779 A | 7/1997 |
| JP | 2006-507839 A | 3/2006 |
| JP | 2008-515772 A | 5/2008 |
| JP | 2009-507482 A | 2/2009 |
| WO | WO 88/00239 A1 | 1/1988 |
| WO | WO 88/01648 A1 | 3/1988 |
| WO | WO 90/04036 A1 | 4/1990 |
| WO | WO 90/05188 A1 | 5/1990 |
| WO | WO 91/08216 A1 | 6/1991 |
| WO | WO 92/03918 A1 | 3/1992 |
| WO | WO 93/12227 A1 | 6/1993 |
| WO | WO 95/17085 A1 | 6/1995 |
| WO | WO 95/24488 A1 | 9/1995 |
| WO | WO 95/24494 A1 | 9/1995 |
| WO | WO 95/24495 A1 | 9/1995 |
| WO | WO 97/05771 A2 | 2/1997 |
| WO | WO 97/07669 A1 | 3/1997 |
| WO | WO 97/09350 A1 | 3/1997 |
| WO | WO 98/54226 A1 | 12/1998 |
| WO | WO 99/11773 A1 | 3/1999 |
| WO | WO 00/30436 A1 | 6/2000 |
| WO | WO 01/00855 A1 | 1/2001 |
| WO | WO 01/26455 A1 | 4/2001 |
| WO | WO 01/77181 A2 | 10/2001 |
| WO | WO 02/22150 A2 | 3/2002 |
| WO | WO 02/30954 A1 | 4/2002 |
| WO | WO 02/072636 A2 | 9/2002 |
| WO | WO 03/035835 A2 | 5/2003 |
| WO | WO 2004/050847 A2 | 6/2004 |
| WO | WO 2007/005786 A2 | 1/2007 |
| WO | WO 2007/029054 A1 | 3/2007 |
| WO | WO 2007/048077 A2 | 4/2007 |
| WO | WO 2007/048122 A2 | 4/2007 |
| WO | WO 2007/091266 A2 | 8/2007 |
| WO | WO 2007/115813 A1 | 10/2007 |
| WO | WO 2008/015339 A2 | 2/2008 |
| WO | WO 2008/028686 A2 | 3/2008 |
| WO | WO 2010/009388 A1 | 1/2010 |
| WO | WO 2010/127939 A1 | 11/2010 |
| WO | WO 2014/125377 A2 | 8/2014 |

OTHER PUBLICATIONS

Harduin-Lepers (2001, Biochimie, 83:727-737).*
Wolfgang, 2002, Molecular Reproduction and Development, vol. 62, pp. 69-72.*
Sutter, 2003, PNAS, vol. 100, pp. 1105-1110.*
Zimecki, 2005, Postepy Hig Med Dosw, 59:309-323, English Abstract.*
Anthony et al., Identification of a receptor required for the anti-inflammatory activity of IVIG. Proc Natl Acad Sci U S A. Dec. 16, 2008;105(50):19571-8.
Boyd et al., The effect of the removal of sialic acid, galactose and total carbohydrate on the functional activity of Campath-1H. Mol Immunol. Dec. 1995;32(17-18):1311-8.
Bremel et al., Alteration of milk composition using molecular genetics. J Dairy Sci. Oct. 1989;72(10):2826-33.
Brunt, Molecular Farming: Transgenic Animals as Bioreactors. Bio/Technology. 1988;6(10):1149-54.
Chiu et al., In vivo targeting function of N-linked oligosaccharides with terminating galactose and N-acetylgalactosamine residues. J Biol Chem. Jun. 10, 1994;269(23):16195-202.
Chuang et al., Elimination of N-linked glycosylation sites from the human IgA1 constant region: effects on structure and function. J Immunol. Jan. 15, 1997;158(2):724-32.
Clark et al., Expression of Human Anti-Hemophilic Factor IX in the Milk of Transgenic Sheep. Biotechnology (N Y). 1989 (7):487-92.
Clark et al., Pharmaceuticals from Transgenic Livestock. Trends Bio Tech. 1987;5:20-4.
Clynes et al., Inhibitory Fc receptors modulate in vivo cytoxicity against tumor targets. Nat Med. Apr. 2000;6(4):443-6.
Davies et al., Expression of GnTIII in a recombinant anti-CD20 CHO production cell line: Expression of antibodies with altered glycoforms leads to an increase in ADCC through higher affinity for FC gamma RIII. Biotechnol Bioeng. Aug. 20, 2001;74(4):288-94.
Ditullio et al., Production of cystic fibrosis transmembrane conductance regulator in the milk of transgenic mice. Biotechnology (N Y). Jan. 1992;10(1):74-7.
Dorai et al., Aglycosylated chimeric mouse/human IgG1 antibody retains some effector function. Hybridoma. Apr. 1991;10(2):211-7.
Edmunds et al., Transgenically produced human antithrombin: structural and functional comparison to human plasma-derived antithrombin. Blood. Jun. 15, 1998;91(12):4561-71.
Fujii et al., Structural heterogeneity of sugar chains in immunoglobulin G. Conformation of immunoglobulin G molecule and substrate specificities of glycosyltransferases. J Biol Chem. Apr. 15, 1990;265(11):6009-18.
Gil et al., Analysis of the N-glycans of recombinant human Factor IX purified from transgenic pig milk. Glycobiology. Jul. 2008;18(7):526-39.
Gordon et al., Production of Human Tissue Plasminogen Activator in Transgenic Mouse Milk. Biotechnology (N Y). 1987 (5):1183-7.
Gottlieb et al., Deficient uridine diphosphate-N-acetylglucosamine:glycoprotein N-acetylglucosaminyltransferase activity in a clone of Chinese hamster ovary cells with altered surface glycoproteins. J Biol Chem. May 10, 1975;250(9):3303-9.
Hand et al., Comparative biological properties of a recombinant chimeric anti-carcinoma mAb and a recombinant aglycosylated variant. Cancer Immunol Immunother. 1992;35(3):165-74.
Harduin-Lepers et al., The human sialyltransferase family. Biochimie. Aug. 2001;83(8):727-37.
Hong et al., Substitution of glutamine by glutamate enhances production and galactosylation of recombinant IgG in Chinese hamster ovary cells. Appl Microbiol Biotechnol. Oct. 2010;88(4):869-76. doi: 10.1007/s00253-010-2790-1. Epub Aug. 3, 2010.
Houdebine, Production of pharmaceutical proteins from transgenic animals. J Biotechnol. May 31, 1994;34(3):269-87.
Humphreys et al., Therapeutic antibody production technologies: molecules, applications, expression and purification. Curr Opin Drug Discov Devel. Mar. 2001;4(2):172-85.
James et al., N-glycosylation of recombinant human interferon-gamma produced in different animal expression systems. Biotechnology (N Y). Jun. 1995;13(6):592-6.
Jefferis et al., Recognition sites on human IgG for Fc gamma receptors: the role of glycosylation. Immunol Lett. 1995;44(2-3):111-7.
Jeong et al., Enhanced sialylation of recombinant erythropoietin in CHO cells by human glycosyltransferase expression. J Microbiol Biotechnol. Dec. 2008;18(12):1945-52.
Jung et al., Aglycosylated IgG variants expressed in bacteria that selectively bind FcgammaRI potentiate tumor cell killing by monocyte-dendritic cells. Proc. Natl Acad Sci U S A. Jan. 12, 2010;107(2):604-9. Epub Dec. 18, 2009. Abstract only.
Kumpel et al., Galactosylation of human IgG monoclonal anti-D produced by EBV-transformed B-lymphoblastoid cell lines is dependent on culture method and affects Fc receptor-mediated functional activity. Hum Antibodies Hybridomas. 1994;5(3-4): 143-51.
Leatherbarrow et al., Effector functions of a monoclonal aglycosylated mouse IgG2a: binding and activation of complement component C1 and interaction with human monocyte Fc receptor. Mol Immunol. 1985;22(4):407-15.

(56) References Cited

OTHER PUBLICATIONS

Li et al., Structure of the altered oligosaccharide present in glycoproteins from a clone of Chinese hamster ovary cells deficient in N-acetylglucosaminyltransferase activity. J Biol Chem. Sep. 25, 1978;253(18):6426-31.
Limonta et al., Production of active anti-CD6 mouse/human chimeric antibodies in the milk of transgenic mice. Immunotechnology. Aug. 1995;1(2):107-13.
Lobuglio et al., Mouse/human chimeric monoclonal antibody in man: kinetics and immune response. Proc Natl Acad Sci U S A. Jun. 1989;86(11):4220-4.
Lund et al., Control of IgG/Fc glycosylation: a comparison of oligosaccharides from chimeric human/mouse and mouse subclass immunoglobulin Gs. Mol Immunol. 1993;30(8):741-8.
Lund et al., Multiple interactions of IgG with its core oligosaccharide can modulate recognition by complement and human Fc gamma receptor I and influence the synthesis of its oligosaccharide chains. J Immunol. 1996;157(11):4963-9.
Lund et al., Oligosaccharide-protein interactions in IgG can modulate recognition by Fc gamma receptors. FASEB J. Jan. 1995;9(1):115-9.
Malaise et al., Evidence for a role of accessible galactosyl or mannosyl residues of Fc domain in the in vivo clearance of IgG antibody-coated autologous erythrocytes in the rat. Clin Immunol Immunopathol. 1990;54(3):469-83.
Mattu et al., The glycosylation and structure of human serum IgA1, Fab, and Fc regions and the role of N-glycosylation on Fc alpha receptor interactions. J Biol Chem. Jan. 23, 1998;273(4):2260-72.
Maynard et al., Antibody engineering. Annu Rev Biomed Eng. 2000;2:339-76.
Meade et al., Expression of recombinant proteins in milk of transgenic animals. Gene Expression Systems. Jan. 1, 1999:399-427.
Mimura et al., Role of Oligosaccharide residues of IgG1-Fc in Fc gamma RIIb binding. J Biol Chem 2001; 276(49): 45539-47.
Mimura et al., The influence of glycosylation on the thermal stability and effector function expression of human IgG1-Fc: properties of a series of truncated glycoforms. Mol Immunol. 2000;37(12-13):697-706.
Mizuochi et al., Structural and numerical variations of the carbohydrate moiety of immunoglobulin G. J Immunol. Nov. 1982;129(5):2016-20.
Mullins et al., Perspectives Series: Molecular Medicine in Genetically engineered Animals. J Clin Invest. Sep. 1996;98(11):537-40.
Nose et al., Biological significance of carbohydrate chains on monoclonal antibodies. Proc Natl Acad Sci USA. 1983;80(21):6632-6.
Onitsuka et al., Enhancement of sialylation on humanized IgG-like bispecific antibody by overexpression of α2,6-sialyltransferase derived from Chinese hamster ovary cells. Appl Microbiol Biotechnol. Apr. 2012;94(1):69-80.
Pollock et al. Transgenic milk as a method for the production of recombinant antibodies. J Immunol Methods. Dec. 10, 1999;231(1-2):147-57.
Pound et al., Aglycosylated chimaeric human IgG3 can trigger the human phagocyte respiratory burst. Mol Immunol. Feb. 1993;30(3):233-41.
Pursel et al., Status of research with transgenic farm animals. J Anim Sci. 1993;71 Suppl 3:10-19.
Rademacher et al., Glycobiology. Annu Rev Biochem. 1988;57:785-838.
Rademacher et al., Immunoglobulin G as a glycoprotein. Biochem Soc Symp. 1986;51:131-48.
Rademacher, Glycosylation as a factor affecting product consistency. Biologicals. Jun. 1993;21(2):103-4.
Raju et al., Species-specific variation in glycosylation of IgG: evidence for the species-specific sialylation and branch-specific galactosylation and importance for engineering recombinant glycoprotein therapeutics. Glycobiology. May 2000;10(5):477-86.
Raju, Terminal sugars of Fc glycans influence antibody effector functions of IgGs. Curr Opin Immunol. Aug. 2008;20(4):471-8. Epub Jul. 17, 2008.
Ross et al., Production and characterization of a novel human recombinant alpha-1-antitrypsin in PER.C6 cells. J Biotechnol. Dec. 31, 2012;162(2-3):262-73.
Rudd et al., Diversification of the IgG molecule by oligosaccharides. Mol Immunol. Dec. 1991;28(12):1369-78.
Sazinsky et al., Aglycosylated immunoglobulin G1 variants productively engage activating Fc receptors. Proc Natl Acad Sci U S A. Dec. 23, 2008;105(51):20167-72. Epub Dec. 12, 2008. Abstract only.
Soulier et al., Expression analysis of ruminant alpha-lactalbumin in transgenic mice: developmental regulation and general location of important cis-regulatory elements. FEBS Lett. Feb. 3, 1992;297(1-2):13-8.
Stanley et al., Chinese hamster ovary cells selected for resistance to the cytotoxicity of phytohemagglutinin are deficient in a UDP-N-acetylglucosamine—glycoprotein N-acetylglucosaminyltransferase activity. Proc Natl Acad Sci U S A. Sep. 1975;72(9):3323-7.
Stanley, Glycosylation mutants of animal cells. Annu Rev Genet. 1984;18:525-52.
Stockwin et al., The role of therapeutic antibodies in drug discovery. Biochem Soc Trans. 2003;31(2):433-6.
Tandai et al., Structural study of the sugar moieties of monoclonal antibodies secreted by human-mouse hybridoma. Arch Biochem Biophys. 1991;291(2):339-48.
Tao et al., Studies of aglycosylated chimeric mouse-human IgG. Role of carbohydrate in the structure and effector functions mediated by the human IgG constant region. J Immunol. Oct. 15, 1989;143(8):2595-601.
Tarentino et al., The release of intact oligosaccharides from specific glycoproteins by endo-beta-N-acetylglucosaminidase H. J Biol Chem. Feb. 10, 1974;249(3):818-24.
Tsuchiya et al., Effects of galactose depletion from oligosaccharide chains on immunological activities of human IgG. J Rheumatol. 1989;16(3):285-90.
Van Kuik-Romeijn et al., Expression of a functional mouse-human chimeric anti-CD19 antibody in the milk of transgenic mice. Transgenic Res. Apr. 2000;9(2):155-9.
Walker et al., Aglycosylation of human IgG1 and IgG3 monoclonal antibodies can eliminate recognition by human cells expressing Fc gamma RI and/or Fc gamma RII receptors. Biochem J. Apr. 15, 1989;259(2):347-53.
Wall, Transgenic Livestock: Progress and Prospects for the Future. Theriogenology. 1996;45:57-68.
Wright et al., Effect of altered CH2-associated carbohydrate structure on the functional properties and in vivo fate of chimeric mouse-human immunoglobulin G1. J Exp Med. Sep. 1, 1994;180(3):1087-96.
Wright et al., Effect of C2-associated carbohydrate structure on Ig effector function: studies with chimeric mouse-human IgG1 antibodies in glycosylation mutants of Chinese hamster ovary cells. J Immunol. Apr. 1, 1998;160(7):3393-402.
Chitlaru et al., Overloading and removal of N-glycosylation targets on human acetylcholinesterase: effects on glycan composition and circulatory residence time. Biochem J. May 1, 2002;363(Pt 3):619-31.
[No Author Listed] Antithrombin (Recombinant) ATryn for Injection. GTC Biotherapeutics, Inc; US Package Insert: Feb. 3, 2009.
[No Author Listed] GTC Provides Update on TG20 Monoclonal Antibody Targeting CD20. Press Release. Mar. 1, 2010. Accessed at http://www.businesswire.com/news/home/20100301006006/en/GTC-Update-TG20-Monoclonal-Antibody-Targeting-CD20.
[No Author Listed], FDA clears GTC's ATryn, first US approved drug made from a transgenic animal. The Pharma Letter. 2009. http://www.thepharmletter.com/article/fda-clears-gtc-s-atryn-first-us-approved-drug-mad. Last accessed Dec. 3, 2014. 2 pages.
[No Author Listed], Recombinant Human Antithrombin (ATryn) GTC Biotherapeutics. 2007. http://www.wikinvest.com/stock/GTC. Last accessed Dec. 3, 2014. 4 pages.

(56) References Cited

OTHER PUBLICATIONS

Alexander et al., Complete sequence of the bovine beta-lactoglobulin cDNA. Nucleic Acids Res. Aug. 25, 1989;17(16):6739.
Alexander et al., Isolation and characterization of the bovine kappa-casein gene. Eur J Biochem. Dec. 15, 1988;178(2):395-401.
Alzari, P.M. et al., Three-Dimensional Structure of Antibodies. Ann. Rev. Immunol. 1988 6: 555-580.
Baguisi et al., Production of goats by somatic cell nuclear transfer. Nat Biotechnol. May 1999;17(5):456-61.
Berry et al., Comparison of recombinant and plasma-derived antithrombin biodistribution in a rabbit model. Thromb Haemost. Aug. 2009;102(2):302-8. doi: 10.1160/TH09-01-0062.
Bertolini et al., The transgenic animal platform for biopharmaceutical production. Transgenic Res. Jun. 2016;25(3):329-43. doi: 10.1007/s11248-016-9933-9. Epub Jan. 28, 2016.
Bird et al,. Single-chain antigen-binding proteins. (1988) Science. 242: 423-426. Abstract only.
Bischoff et al., A 17.6 kbp region located upstream of the rabbit WAP gene directs high level expression of a functional human protein variant in transgenic mouse milk. FEBS Lett. Jul. 6, 1992;305(3):265-8.
Björk et al., Decreased affinity of recombinant antithrombin for heparin due to increased glycosylation. Biochem J. Sep. 15, 1992;286( Pt 3):793-800.
Blanchard et al., N-glycosylation and biological activity of recombinant human alpha1-antitrypsin expressed in a novel human neuronal cell line. Biotechnol Bioeng. Sep. 2011;108(9):2118-28. doi: 10.1002/bit.23158. Epub Apr. 20, 2011.
Bock et al., Cloning and expression of the cDNA for human antithrombin III. Nucleic Acids Res. Dec. 20, 1982;10(24):8113-25.
Borsig et al., Heparin and cancer revisited: mechanistic connections involving platelets, P-selectin, carcinoma mucins, and tumor metastasis. Proc Natl Acad Sci U S A. Mar. 13, 2001;98(6):3352-7.
Bosques et al., Chinese hamster ovary cells can produce galactose-α-1,3-galactose antigens on proteins. Nat Biotechnol. Nov. 2010;28(11):1153-6.
Brink et al., Developing Efficient Strategies for the Generation of Transgenic Cattle Which Produce Biopharmaceuticals in Milk. Theriogenology. 2000;53:139-48.
Brown, rAAt (inhaled) Arriva/Hyland Immuno. Curr Opin Mal Ther. Feb. 2006;8(1):76-82.
Bühler et al., Rabbit beta-casein promoter directs secretion of human interleukin-2 into the milk of transgenic rabbits. Biotechnology (N Y). Feb. 1990;8(2):140-3.
Cammuso et al., Hormonal induced lactation in transgenic goats. Anim Biotechnol. 2000;11(1):1-17.
Campbell et al., Comparison of the whey acidic protein genes of the rat and mouse. Nucleic Acids Res. Nov. 26, 1984;12(22):8685-97.
Carter, Introduction to current and future protein therapeutics: a protein engineering perspective. Exp Cell Res. May 15, 2011;317(9):1261-9. Doi: 10.1016/j.yexcr.2011.02.013. Epub Mar. 1, 2011.
Carton et al., Codon engineering for improved antibody expression in mammalian cells. Protein Expr Purif. Oct. 2007;55(2):279-86. Epub Jun. 16, 2007.
Castilla et al., Engineering passive immunity in transgenic mice secreting virus-neutralizing antibodies in milk. Nat Biotechnol. Apr. 1998;16(4):349-54.
Castro et al., Transgenic rabbits for the production of biologically-active recombinant proteins in the milk. Genet Anal. Nov. 1999;15(3-5):179-87.
Chada et al., Tissue- and stage-specific expression of a cloned adult beta globin gene in transgenic mice. Prog Clin Biol Res. 1985;191:305-19.
Chindemi et al., Biodistribution of covalent antithrombin-heparin complexes. Thromb Haemost. Apr. 2006;95(4):629-36.
Chitlaru et al., Modulation of circulatory residence of recombinant acetylcholinesterase through biochemical or genetic manipulation of sialylation levels. Biochem J. Dec. 15, 1998;336 (Pt 3):647-58.

Church et al., Embryo manipulation and gene transfer in livestock. Can J Anim Schi Sep. 1985;65:527-538.
Clark, The mammary gland as a bioreactor: expression, processing, and production of recombinant proteins. J Mammary Gland Biol Neoplasia. Jul. 1998;3(3):337-50. Review.
Colcher D, et al., Effects of Genetic Engineering on the Pharmacokinetics of Antibodies. QJ Nucl Med 1999; 43:132-9.
Cole et al. Glycosylation Patterns of Human Proteins Expressed in Transgenic Goat Milk. Journal of Cellular Biochemistry. 1994, Suppl. 18D, p. 265, Ab. U100, published online Feb. 19, 1994.
Colman, Dolly, Polly and other 'ollys': likely impact of cloning technology on biomedical uses of livestock. Genet Anal. Nov. 1999;15(3-5):167-73.
Dai et al., Targeted Disruption of the α1,3-Galactosyltransferase Gene in Cloned Pigs. Nature Biotechnology. Mar. 2002;20:251-5.
Dale et al., Antithrombin III does not have bound glucocerebroside. Biochim Biophys Acta. Jul. 28, 1981;669(2):260-2.
Dale et al., High-level expression of the rat whey acidic protein gene is mediated by elements in the promoter and 3' untranslated region. Mol Cell Biol. Mar. 1992;12(3):905-14.
Dalrymple et al., Genetically modified livestock for the production of human proteins in milk. Biotechnol Genet Eng Rev. 1998;15:33-49. Review.
Davis, G. T. et al., Single Chain Antibody (SCA) Encoding Genes: One-Step Construction and Expression in Eukaryotic Cells. Bio/Technol. 1991 9: 165-69.
Del Mar et al., Effect of oxidation of methionine in a peptide substrate for human elastases: a model for inactivation of alpha 1-protease inhibitor. Biochem Biophys Res Commun. May 28, 1979;88(2):346-50.
Ditullio et al., High level expression of tissue plasminogen activator using the goat beta casein promoter. FASEB J. May 1993;7(7):A1223. Abstract No. 993.
Drohan, The past, present and future of transgenic bioreactors. Thromb Haemost. Jul. 1997;78(1):543-7.
Ebert et al., Transgenic production of a variant of human tissue-type plasminogen activator in goat milk: generation of transgenic goats and analysis of expression. Biotechnology (N Y). Sep. 1991;9(9):835-8.
Echelard et al., Chapter 11. The First Biopharmaceutical from Transgenic Animals: ATryn®. In Modern Biopharmaceuticals: Design, Development and Optimization, eds. J. Knablein and R. H. Miler. 2005;1-26.
Echelard et al., Chapter 24: Protein production in transgenic animals. S.C. Makrides, ed., Gene Transfer and Expression in Mammalian Cells. 2003:625-639.
Echelard, Recombinant protein production in transgenic animals. Curr Opin Biotechnol. Oct. 1996;7(5):536-40.
Edmunds et al., Tissue Specific and Species Differences in the Glycosylation Pattern of Antithrombin III, Journal of Cellular Biochemistry, Abstract U102, pp. 265 (1994).
Ehlers, Immune-modulating effects of alpha-1 antitrypsin. Biol Chem. Oct. 2014;395(10):1187-93. doi: 10.1515/hsz-2014-0161.
Fan et al., Heterogeneity of recombinant human antithrombin III expressed in baby hamster kidney cells. Effect of glycosylation differences on heparin binding and structure. J Biol Chem. Aug. 15, 1993;268(23):17588-96.
Federspiel G, et al., (1991), Hybridoma Antibody Production In Vitro in Type II SerumFree Medium Using Nutridoma-SP Supplements: Comparisons With In Vivo Methods, J Immunol Methods 145(1-2):213-221.
Fernandes, Demonstrating Comparability of Antibody Glycosylation during Biomanufacturing. European Biopharmaceutical Review. Summer 2005: 106-10.
Fiat et al., Caseins of various origins and biologically active casein peptides and oligosaccharides: structural and physiological aspects. Mol Cell Biochem. May 4, 1989;87(1):5-30.
Fliedl et al., Novel Human Renal Proximal Tubular Cell Line for the Production of Complex Proteins. Journal of Biotechnology. 2014;176:29-39.
Fyfe et al., Antithrombin-α for the Prophylaxis of Venous Thrombosis in Congenital Antithrombin Deficiency. Expert Rev. Hematol. 2009;2(5):499-507.

(56) References Cited

OTHER PUBLICATIONS

Ghetie et al., FcRn: the MHC class I-related receptor that is more than an IgG transporter. Immunol Today. Dec. 1997;18(12):592-8.
Goodarzi et al., Decreased branching, increased fucosylation and changed sialylation of alpha-1-proteinase inhibitor in breast and ovarian cancer. Clin Chim Acta. May 15, 1995;236(2):161-71.
Gorodetsky et al., Isolation and characterization of the Bos taurus beta-casein gene. Gene. Jun. 15, 1988;66(1):87-96.
Greenberg et al., Expression of biologically active heterodimeric bovine follicle-stimulating hormone in milk of transgenic mice. Proc Natl Acad Sci U S A. Oct. 1, 1991;88(19):8327-31.
Guile et al., A rapid high-resolution high-performance liquid chromatographic method for separating glycan mixtures and analyzing oligosaccharide profiles. Anal Biochem. Sep. 5, 1996;240(2):210-26.
Gunzburg et al., A mammary-specific promoter directs expression of growth hormone not only to the mammary gland, but also to Bergman glia cells in transgenic mice. Mol Endocrinol. Jan. 1991;5(1):123-33. Abstract Only.
Hall et al., Organization and sequence of the human alpha-lactalbumin gene. Biochem J. Mar. 15, 1987;242(3):735-42.
Hansson et al., Expression and characterization of biologically active human extracellular superoxide dismutase in milk of transgenic mice. J Biol Chem. Feb. 18, 1994;269(7):5358-63.
Hauschild et al., Efficient Generation of a Biallelic Knockout in Pigs Using Zinc-Finger Nucleases. PNAS. Jul. 19, 2011;108(29):12013-12017.
Heavey, U.S. Approves First Drug from DNA-Altered Animals. Reuters Science News. Http://reuters.com/article/us-gtc-atryn-idUSTRE51540E20090206. [dated Feb. 6, 2009; last accessed May 16, 2017].
Heimburger et al. Proteinase Inhibitors of Human Plasma. Proc. Int. Res. Conf. Proteinase Inhibitors. 1970: 1-21.
Hennighausen et al., Characterization and cloning of the mRNAs specific for the lactating mouse mammary gland. Eur J Biochem. Jun. 15, 1982;125(1):131-41.
Hobbs et al., Sequence of rat alpha- and gamma-casein mRNAs: evolutionary comparison of the calcium-dependent rat casein multigene family. Nucleic Acids Res. Dec. 20, 1982;10(24):8079-98.
Hodoniczky et al., Control of recombinant monoclonal antibody effector functions by Fc N-glycan remodeling in vitro. Biotechnol Prog. Nov.-Dec. 2005;21(6):1644-52.
Holliger et al., Diabodies: small bivalent and bispecific antibody fragments. (1993) Proc. Natl. Acad. Sci. USA 90: 6444-6448.
Houdebine et al., Transgenic animal bioreactors. Transgenic Res. 2000;9(4-5):305-20.
Houdebine, The production of pharmaceutical proteins from the milk of transgenic animals. Reprod Nutr Dev. 1995;35(6):609-17.
Hubbard et al., Recombinant DNA-produced alpha 1-antitrypsin administered by aerosol augments lower respiratory tract antineutrophil elastase defenses in individuals with alpha 1-antitrypsin deficiency. J Clin Invest. Oct. 1989;84(4):1349-54.
Hubbard et al., Strategies for aerosol therapy of alpha 1-antitrypsin deficiency by the aerosol route. Lung. 1990;168 Suppl:565-78.
Hughes, 2009 FDA drug approvals. Nat Rev Drug Discov. Feb. 2010;9(2):89-92. doi:10.1038/nrd3101.
Huston et al., Protein engineering of antibody binding sites: recovery of specific activity in an anti-digoxin single-chain Fv analogue produced in *Escherichia coli*. (1988) Proc. Natl. Acad. Sci. USA 85: 5879-5883.
Jänne et al., Transgenic animals as bioproducers of therapeutic proteins. Ann Med. Aug. 1992;24(4):273-80.
Jänne et al., Transgenic bioreactors. Int J Biochem. Jul. 1994;26(7):859-70.
Johnson et al., Crystal structure of monomeric native antithrombin reveals a novel reactive center loop conformation. J Biol Chem. Nov. 17, 2006;281(46):35478-86. Epub Sep. 13, 2006.
Johnson et al., Human alpha-1-proteinase inhibitor mechanism of action: evidence for activation by limited proteolysis. Biochem Biophys Res Commun. Sep. 7, 1976;72(1):33-9.
Jones et al., The rat casein multigene family. Fine structure and evolution of the beta-casein gene. J Biol Chem. Jun. 10, 1985;260(11):7042-50.
Joosten et al., Alpha-1-anti-trypsin-Fc fusion protein ameliorates gouty arthritis by reducing release and extracellular processing of IL-1β and by the induction of endogenous IL-1Ra. Ann Rheum Dis. Jul. 14, 2015. pii:annrheumdis-2014-206966. doi: 10.1136/annrheumdis-2014-206966. [Epub ahead of print].
Karnaukhova et al., Recombinant human alpha-1 proteinase inhibitor: towards therapeutic use. Amino Acids. Jun. 2006;30(4):317-32. Epub May 26, 2006.
Khodarovich et al., Expression of Eukaryotic Recombinant Proteins and Deriving Them from the Milk of Transgenic Animals. Applied Biology and Microbiology. 2013;49(9);711-22.
Kim et al., Catabolism of the murine IgG1 molecule: evidence that both CH2-CH3 domain interfaces are required for persistence of IgG1 in the circulation of mice. Scand J Immunol. 1994;40(4):457-65.
Ko et al., Production of biologically active human granulocyte colony stimulating factor in the milk of transgenic goat. Transgenic Res. Jun. 2000;9(3):215-22.
Köhler et al., Continuous cultures of fused cells secreting antibody of predefined specificity. Nature. Aug. 7, 1975;256(5517):495-7.
Kolb et al., Virus-neutralizing monoclonal antibody expressed in milk of transgenic mice provides full protection against virus-induced encephalitis. J Virol. Mar. 2001;75(6):2803-9.
Lantto et al., Chain Shuffling to Modify Properties of Recombinant Immunoglobulins. Methods Mol. Biol. (2002) 178: 303-316.
Lathe et al., Novel products from livestock. Exploiting New Technologies in animal breeding: Genetic developments. 1986:91-102.
Lee et al., Effect of recombinant α1-antitrypsin Fc-fused (AAT-Fc)protein on the inhibition of inflammatory cytokine production and streptozotocin-induced diabetes. Mol Med. May 20, 2013;19:65-71. doi:10.2119/molmed.2012.00308.
Lee et al., Expression of the Rat β-Casein Gene in Transgenic Mice. Abstract presented at 26th Annual Meeting of the American Society for Cell Biology. Dec. 1986;313a. Abstract 1161.
Lee et al., Production of Recombinant Human Von Zillebrand Factor in the Milk of Transgenic Pigs. J of Reprod. Dev. 2009;55(5):484-490.
Leitner et al., Recombinant human antithrombin inhibits thrombin formation and interleukin 6 release in human endotoxemia. Clin Pharmacol Ther. Jan. 2006;79(1):23-34.
Lewis, Expanding the clinical indications for α(1)-antitrypsin therapy. Mol Med. Sep. 7, 2012;18:957-70. doi: 10.2119/molmed. 2011.00196.
Li et al., Biallelic Knockout of the α-1,3 Galactosyltransferase Gene in Procine Liver-Derived Cells Using Zinc Finger Nucleases. Journal of Surgical Research. 2013;181:E39-E45.
Logan, Transgenic animals: beyond 'funny milk'. Curr Opin Biotechnol. Oct. 1993;4(5):591-5.
Loveil-Badge et al., Transgenic animals: new advances in the field. Nature. Jun. 20, 1985;315:628-29.
Lusch et al., Development and Analysis of Alpha 1-Antitrypsin Neoglycoproteins: The Impact of Additional N-Glycosylation Sites on Serum Half-Life. Molecular Pharmaceutics. Jul. 1, 2013;10(7)2616-29.
Maga et al., Mammary Gland Expression of Transgenes and the Potential for Altering the Properties of Milk. Nature Biotechnology. 1995;(13):1452-7.
Magdelaine-Beuzelin et al., Structure-function relationships of the variable domains of monoclonal antibodies approved for cancer treatment. Crit Rev Oncol Hematol. Dec. 2007;64(3):210-25.
Meade et al., Bovine alpha S1-casein gene sequences direct high level expression of active human urokinase in mouse milk. Biotechnology (N Y). May 1990;8(5):443-6.
Melican et al., Effect of serum concentration, method of trypsinization and fusion/activation utilizing transfected fetal cells to generate transgenic dairy goats by somatic cell nuclear transfer. Theriogenology. Apr. 1, 2005;63(6):1549-63.

(56) References Cited

OTHER PUBLICATIONS

Menache et al., Evaluation of the Safety, Recovery, Half-Life, and Clinical Efficacy of Antithrombin III (Human) in Patients with Hereditary Antithrombin III Deficiency. Blood. 1990, vol. 75, pp. 33-39.

Mercier et al., Structure and function of milk protein genes. J Dairy Sci. Oct. 1993;76(10):3079-98.

Morgan et al., Designing Biobetter Monoclonal Antibody Therapeutics by Glycoengineering. International Pharmaceutical Industry. 2009. 5 pages.

Moura et al., Production of Recombinant Proteins in Milk of Transgenic and Non-Transgenic Goats. Brazilian Archives of Biology and Technology. Sep. 2011;54(5):927-38.

Packer et al., A general approach to desalting oligosaccharides released from glycoproteins. Glycoconj J. Aug. 1998;15(8):737-47.

Padlan, E. A., Anatomy of the Antibody Molecule, Mol. Immunol. 31(3): 169-217 (1994).

Pal et al., Pharmacology and clinical applications of human recombinant antithrombin. Expert Opin Biol Ther. Jul. 2010;10(7):1155-68. doi: 10.1517/14712598.2010.495713.

Paleyanda et al., Regulation of human protein C gene expression by the mouse WAP promoter. Transgenic Res. Nov. 1994;3(6):335-43.

Paleyanda et al., Secretion of human furin into mouse milk. J Biol Chem. Jun. 13, 1997;272(24):15270-4.

Paleyanda et al., Transgenic pigs produce functional human factor VIII in milk. Nat Biotechnol. Oct. 1997;15(10):971-5.

Palmiter et al., Germ-line transformation of mice. Annu Rev Genet. 1986;20:465-99. Review.

Pangburn et al., Molecular mechanisms of target recognition in an innate immune system: interactions among factor H, C3b, and target in the alternative pathway of human complement. J Immunol. May 1, 2000;164(9):4742-51.

Pannell et al., Isolation and properties of human plasma alpha-1-proteinase inhibitor. Biochemistry. Dec. 17, 1974;13(26):5439-45.

Pantschenko et al., Establishment and characterization of a caprine mammary epithelial cell line (CMEC). In Vitro Cell Dev Biol Anim. Jan. 2000;36(1):26-37. Abstract only.

Park et al., Recombinant Human Erythropoietin Produced in Milk of Transgenic Pigs. Journal of biotechnology. Apr. 10, 2006;122(3):362-71.

Patton et al., Intramammary infusion technique for genetic engineering of the mammary gland. Journal of dairy science. 1984;(67):1323-6.

Pearse et al., Chapter 12: Anti-Xenograft Immune Responses in α1,3-Galactosyltransferase Knock-Out Mice. Inα-Gal and Anti-Gal. 1999: 281-310.

Pemberton et al., Inhaled recombinant alpha 1-antitrypsin ameliorates cigarette smoke-induced emphysema in the mouse. COPD. Jun. 2006;3(2):101-8.

Persuy et al., High expression of the caprine beta-casein gene in transgenic mice. Eur J Biochem. May 1, 1992;205(3):887-93.

Piletz et al., Biochemical characterization of a novel whey protein from murine milk. J Biol Chem. Nov. 25, 1981;256(22):11509-16.

Poljak, R. J. et al., Production and structure of diabodies (1994) Structure 2: 1121-1123.

Qasba et al., Similarity of the Nucleotide Sequences of Rat α-lactalbumin and Chicken Lysozyme Genes. Nature. Mar. 22, 1984;308:377-80.

Rademacher et al., The role of IgG glycoforms in the pathogenesis of rheumatoid arthritis. Springer Semin Immunopathol. 1988;10(2-3):231-49.

Raju, Glycosylation Variations with Expression Systems. BioProcess International. Apr. 2003; 44-53.

Richards et al., Construction and preliminary characterization of the rat casein and alpha-lactalbumin cDNA clones. J Biol Chem. Jan. 10, 1981;256(1):526-32.

Roberts et al., Cloning of the goat beta-casein-encoding gene and expression in transgenic mice. Gene. Nov. 16, 1992;121(2):255-62.

Salamone et al., High level expression of bioactive recombinant human growth hormone in the milk of a cloned transgenic cow. J Biotechnol. Jul. 13, 2006;124(2):469-72. Epub May 23, 2006.

Samiec et al., Transgenic Mammalian Species, Generated by Somatic Cell Cloning, in Biomedicine, Biopharmaceutical Industry and Human Nutrition/Dietetics—Recent Acheivements. Polish Journal of Veterinary Sciences. 2011;14(2):317-28.

Schneider, Texas Researchers Develop 4 Gene-Altered Calves. The New York Times National. Jun. 8, 1990.

Schnieke et al., Human factor IX transgenic sheep produced by transfer of nuclei from transfected fetal fibroblasts. Science. 1997;278:2130-3.

Schuurman et al., The inter-heavy chain disulfide bonds of IgG4 are in equilibrium with intra-chain disulfide bonds. Mol Immunol. Jan. 2001;38(1):1-8.

Seamark, Progress and emerging problems in livestock transgenesis: a summary perspective. Reprod Fertil Dev. 1994;6(5):653-7.

Selgrath et al., Collection and transfer of microinjectable embryos from dairy goats. Theriogenology. 1990;34(6):1195-205.

Shahaf et al., α-1-antitrypsin gene delivery reduces inflammation, increases T-regulatory cell population size and prevents islet allograft rejection. Mol Med. Sep.-Oct. 2011;17(9-10):1000-11. doi: 10.2119/molmed.2011.00145. Epub Jun. 9, 2011.

Shamay et al., Expression of the whey acidic protein in transgenic pigs impairs mammary development. Transgenic Res. May 1992;1(3):124-32.

Shim, One target, different effects: a comparison of distinct therapeutic antibodies against the same targets. Exp Mol Med. Oct. 31, 2011;43(10):539-49. doi: 10.3858/emm.2011.43.10.063.

Simons et al., Gene Transfer into Sheep. Bio/Technology. 1998;6:179-83.

Smith, Commercial exploitation of transgenics. Biotechnol Adv. 1994;12(4):679-86.

Sola et al., Transgenic mice secreting coronavirus neutralizing antibodies into the milk. J Virol. May 1998;72(5):3762-72.

Stewart et al., Nucleotide sequences of bovine alpha S1- and kappa-casein cDNAs. Nucleic Acids Res. May 11, 1984;12(9):3895-907.

Stinnakre et al., The bovine alpha-lactalbumin promoter directs expression of ovine trophoblast interferon in the mammary gland of transgenic mice. FEBS Lett. Jun. 17, 1991;284(1):19-22.

Stromqvist et al., Recombinant human extracellular superoxide dismutase produced in milk of transgenic rabbits. Transgenic Res. Jul. 1997;6(4):271-8.

Suen et al., Transient expression of an IL-23R extracellular domain Fc fusion protein in CHO vs. HEK cells results in improved plasma exposure. Protein Expr Purif. May 2010;71(1):96-102. doi: 10.1016/j.pep.2009.12.015. Epub Jan. 4, 2010.

Sumar et al., Analysis of glycosylation changes in IgG using lectins. J Immunol Methods. Jul. 20, 1990;131(1):127-36.

Tan et al., Influence of the hinge region on complement activation, C1q binding, and segmental flexibility in chimeric human immunoglobulins. Proc Natl Acad Sci U S A. Jan. 1990;87(1):162-6.

Tebbutt, Technology evaluation: transgenic alpha-1-antitrypsin (AAT), PPL therapeutics. Curr Opin Mol Ther. Apr. 2000;2(2):199-204.

Thepot et al., Rabbit whey acidic protein gene upstream region controls high-level expression of bovine growth hormone in the mammary gland of transgenic mice. Mol Reprod Dev. Nov. 1995;42(3):261-7.

Todorovska et al., Design and application of diabodies, triabodies and tetrabodies for cancer targeting. J Immunol Methods. Feb. 1, 2001;248(1-2):47-66.

Toyama et al., Quantitative structural characterization of local N-glycan microheterogeneity in therapeutic antibodies by energy-resolved oxonium ion monitoring. Anal Chem. Nov. 20, 2012;84(22):9655-62.

Vilotte et al., Complete nucleotide sequence of bovine alpha-lactalbumin gene: comparison with its rat counterpart. Biochimie. Jun.-Jul. 1987;69(6-7):609-20.

Waldmann, Monoclonal antibodies in diagnosis and therapy. Science. Jun. 21, 1991;252(5013):1657-62.

(56) References Cited

OTHER PUBLICATIONS

Wall et al., High-level synthesis of a heterologous milk protein in the mammary glands of transgenic swine. Proc Natl Acad Sci U S A. Mar. 1, 1991;88(5):1696-700.
Ward et al., Binding activities of a repertoire of single immunoglobulin variable domains secreted from *Escherichia coli*. (1989) Nature 341: 544-546.
Ward et al., The commercial and agricultural applications of animal transgenesis. Mol Biotechnol. Oct. 1995;4(2):167-78. Review.
Wei et al., Production of human surfactant protein C in milk of transgenic mice. Transgenic Res. Jul. 1995;4(4):232-40.
Weidle et al., Genes encoding a mouse monoclonal antibody are expressed in transgenic mice, rabbits and pigs. Gene. Feb. 15, 1991;98(2):185-91.
Werner et al., Glycosylation of therapeutic proteins in different production systems. Acta Paediatr. Apr. 2007;96(455):17-22.
Whitlow M.B. et al., An Improved Linker for Single-Chain Fv With Reduced Aggregation and Enhanced Proteolytic Stability. Protein Eng. (1993) 6(8): 989-995.
Wilmut et al., A revolution in animal breeding. New Scientist. Jul. 7, 1988:56-9.
Wilmut et al., Production of pharmaceutical proteins in milk. Experientia. Sep. 15, 1991;47(9):905-12. Review.
Wilmut et al., Strategies for production of pharmaceutical proteins in milk. Reprod Fertil Dev. 1994;6(5):625-30. Review.
Wom et al., Stability Engineering of Antibody Single-Chain Fv fragments. J Mol Biol 2001; 305: 989-1010.
Yom et al., Genetic engineering of milk composition: modification of milk components in lactating transgenic animals. Am J Clin Nutr. Aug. 1993;58(2 Suppl):299S-306S.
Yu-Lee et al., Evolution of the Casein Multigene Family: Conserved Sequences in the 5' Flanking and Exon Regions. Nucleic Acids Research. Feb. 25, 1986;14(4):1883-902.
Yu-Lee et al., The rat casein multigene family. I. Fine structure of the gamma-casein gene. J Biol Chem. Sep. 10, 1983;258(17):10794-804.
Yung et al., Complete absence of the αGal xenoantigen and isoglobotrihexosylceramide in α1,3galactosyltransferase knock-out pigs. Xenotransplantation. May-Jun. 2012;19(3):196-206.
Zhang et al., Functional Recombinant Human Anti-HBV Antibody Expressed in Milk of Transgenic Mice. Transgenic Res. 2012;21:1085-91.
Zhou et al., Effect of genetic background on glycosylation heterogeneity in human antithrombin produced in the mammary gland of transgenic goats. J Biotechnol. Apr. 20, 2005;117(1):57-72.
Ziomek, Commercialization of Proteins Produced in the Mammary Gland. Theriogenology. 1998;49:139-44.
[No Author Listed] GTC Biotherapeutics and LFB Biotechnologies Enter Strategic Collaboration for Recombinant Plasma Proteins and Monoclonal Antibodies. Press Release; Oct. 2, 2006. Last accessed from <https://www.businesswire.com/news/home/20061002005515/en/GTC-Biotherapeutics-LFB-Biotechnologies-Enter-Strategic-Collaboration> on Jan. 19, 2018.
[No Author Listed] GTC Biotherapeutics Expects CHMP to Issue Negative Opinion on ATryn(R). Press Release; Feb. 23, 2006. Last accessed from <http://www.businesswire.com/news/home/20060223005411/en/GTC-Biotherapeutics-Expects-CHMP-Issue-Negative-Opinion> on Nov. 30, 2015.
[No Author Listed] Herceptin® Trastuzumab. Genentech, Inc.; US Package Insert. Sep. 1998.
[No Author Listed] Trastuzumab. Wikipedia. Oct. 30, 2012.
[No Author Listed], Securities and Exchange Commission Form 10-K for the fiscal year ended Dec. 29, 2002. GTC Biotherapeutics, Inc. Filed Mar. 6, 2008. Excerpt.
Bendig, Humanization of Rodent Monoclonal Antibodies by CDR Grafting. Companion to Methods in Enzymology. 1995;8:83-93.
Bookman et al., Evaluation of monoclonal humanized anti-HER2 antibody, trastuzumab, in patients with recurrent or refractory ovarian or primary peritoneal carcinoma with overexpression of HER2: a phase II trial of the Gynecologic Oncology Group. J Clin Oncol. Jan. 15, 2003;21(2):283-90.
Campbell et al., Nuclear-cytoplasmic interactions during the first cell cycle of nuclear transfer reconstructed bovine embryos: implications for deoxyribonucleic acid replication and development. Biology of Reproduction. 1993;49(5):933-42.
Clark et al., Assessing unintended effects of a mammary-specific transgene at the whole animal level in host and non-target animals. Transgenic Research. 2014;23:245-256.
Clark et al., Protein Purification of Bio-Synthetic Spider Silk. Utah State University. Apr. 2012. Available online at https://works.bepress.com/candace_clark/2/. Last accessed on Jan. 30, 2018. 2 pages.
Defazio-Eli et al., Quantitative assays for the measurement of HER1-HER2 heterodimerization and phosphorylation in cell lines and breast tumors: applications for diagnostics and targeted drug mechanism of action. Breast Cancer Res. Apr. 15, 2011;13(2):R44.
Echelard, Production in the Milk of Transgenic Animals A Validated, Cost-Effective Approach for the Manufacturing of Complex Recombinant Protein. EuroBio 2009. 34 pages.
Gao, The Effect of Alpha 1-Antitrypsin on Ischemia-Reperfusion Injury in Lung Transplantation. University of Toronto, Department of Physiology. 2012. 89 pages.
Gee et al., Human breast cancer tumor models: molecular imaging of drug susceptibility and dosing during HER2/neu-targeted therapy. Radiology. Sep. 2008;248(3):925-35.
Goeddel, Systems for Heterologous Gene Expression. Methods in Enzymology. 1990;185:3-7.
Hiatt et al., Production of antibodies in transgenic plants. Nature. Nov. 2, 1989;342(6245):76-8.
Hobbs et al., Complex Hormonal Regulation of Rat Casein Gene Expression. Journal of Biological Chemistry. Apr. 10, 1982;257(7):3598-605.
Horwitz et al., Secretion of functional antibody and Fab fragment from yeast cells. Proc Natl Acad Sci U S A. Nov. 1988;85(22):8678-82.
Houde et al., Post-translational modifications differentially affect IgG1 conformation and receptor binding. Molecular & Cellular Proteomics. Aug. 2010;9(8):1716-28.
Jain et al., Targeted inactivation of Gα1 does not alter cardiac function or β-adrenergic sensitivity. Am J Physiol Heart Circ Physiol. 2001;280:H569-H575.
Jones et al., Ectopic Correction of Ornithine Transcarbamylase Deficiency in Sparse Fur Mice. Journal of Biological Chemistry. Aug. 25, 1990;265(24):14684-14690.
Kasinathan et al., Effect of Fibroblast Donor Cell Age and Cell Cycle on Development of Bovine Nuclear Transfer Embryos in Vitro. Biology of Reproduction. 2001;64:1487-1493.
Kerr et al., The bladder as a bioreactor: Urothelium production and secretion of growth hormone into urine. Nature Biotechnology. Jan. 1998;16(1):75-9.
Lee et al., Production of biomedical proteins in the milk of transgenic dairy cows: the state of the art. Journal of Controlled Release. 1994;29:213-231.
Liao et al., Design of Transgenes for Efficient Expression of Active Chimeric Proteins on Mammalian Cells. Biotechnology and Bioengineering. May 20, 2001;73(4):313-23.
Maga et al., Expression of human lysozyme mRNA in the mammary gland of transgenic mice. Transgenic Research. 1994;3:36-42.
McGrane et al., Matebolic control of gene expression: in vivo studies with transgenic mice. Trands Biochem Sci. Jan. 1992;17(1):40-44.
Mourey et al., Antithrombin III: structural and functional aspects. Biochimie. 1990;72:599-608.
Nagy et al., Targeted mutagenesis: analysis of phenotype without germ line transmission. J Clin Invest. Mar. 15, 1996;97(6):1360-1365.
Niemann et al., Transgenic Livestock: premises and promises. Animal Reproduction Science. 2000;60-61:277-293.
Okayama et al., A cDNA Cloning Vector That Permits Expresson of cDNA Inserts in Mammalian Cells. Melecular and Cellular Biology. Feb. 1983;3(2):280-289.

(56) References Cited

OTHER PUBLICATIONS

Ongeri et al., Development of Goat Embryos after in Vitro Fertilization and Parthenogenetic Activation by Different Methods. Theriogenology. 2001;55:1933-1945.

Papac et al., A high-throughput microscale method to release N-linked oligosaccharides from glycoproteins for matrix-assisted laser desorption/ionization time-of-flight mass spectrometric analysis.Glycobiology. 1998;8(5):445-454.

Paul, Fundamental Immunology. 3rd edition. Chapter 9: Structure and Function of Immunoglobulins. 1993:292-295.

Reff et al., Depletion of B cells in vivo by a chimeric mouse human monoclonal antibody to CD20. Blood. Jan. 15, 1994;83(2):435-45.

Regalado, Building a Better Goat. MIT Technology Review. Oct. 20, 2010. Available online at https://www.technologyreview.com/s/421268/building-a-better-goat/. Last accessed on Mar. 19, 2014. 2 pages.

Sakai et al., Recombination and transcription of the endogenous Ig heavy chain locus is effected by the Ig heavy chain itronic enhancer core region in the absence of the matrix attachment regions. Proc. Natl. Acad. Sci. USA. Feb. 1999;96:1526-1531.

Shen et al., Tissue-Specific Regulation of Human α1-Antitrypsin Gene Expression in Transgenic Mice. DNA. 1989;8(2):101-108.

Shimada et al., Correction of ornithine transcarbamylase (OTC) deficiency in spf-ash mice by introduction of rat OTC gene. FEBS letters. Feb. 1991;279(1):198-200.

Smith et al., Pulomonary Disposition and Clearance of Aerosolized Alpha-1-Proteinase Inhibitor Administered to Dogs and to Sheep. J Clin Invest. Oct. 1989;84:1145-1154.

Stieger et al., Self assembly of immunoglobulins in the cytoplasm of the alga acetabularia mediterranea. Plant Science. 1991;73:181-89.

Thomann et al., Fc-galactosylation modulates antibody-dependent cellular cytotoxicity of therapeutic antibodies.Molecular Immunology. 2016;73:69-75.

Wells et al., Production of Cloned Calves Following Nuclear Transfer with Cultured Adult Mural Granulosa Cells. Biology of Reproduction. 1999;60:996-1005.

Wilkins et al., Isolation of Recombinant Proteins From Milk Journal of Cellular Biochemistry. 1992;49:333-338.

Wright et al., High Level Expression of Active Human Alpha-1-Antitrypsin in the Milk of Transgenic Sheep. Biotechnology. 1991;9:830-834.

Yong et al., Nuclear-Cytoplasmic Interaction and Development of Goat Embryos Reconstructed by Nuclear Transplantation: Production of Goats by Serially Cloning Embryos. Biology of Reproduction. 1998;58:266-269.

Zbikowska et al., The use of uromodulin promoter to target production of recombinant proteins into urine of transgenic animals. Transgenic Research. 2002;11:425-435.

Zbikowska et al., Uromodulin promoter directs high-level expression of biologically active human α1-antitrypsin into mouse urine. Biochem J. 2002;365:7-11.

\* cited by examiner

```
Query:   1   MTRTSLKKKFFSCCVLIFLLFAIICVWKEKKKGNYYEFLKLQNKEYQMLQGLEKLAMSSS   60
             M T+LKKKF SCCVL+FLLFA+ICVWKEKKKG+YY+  KLQ KE+Q+L+ L KLAM S
Sbjct:   1   MIHTNLKKKF-SCCVLVFLLFAVICVWKEKKKGSYYDSFKLQTKEFQVLKSLGKLAMGSD   59

Query:  61   SQPGSSSSTHNPQKNIQALGG----PKAKLGATFQVWDKDSSSKNLAPRLQTIRKNYLNM  116
             SQ SSSST +P +  Q LG      KAK  A+FQVW+KDSSSKNL PRLQ I KNYL+M
Sbjct:  60   SQSVSSSSTQDPHRGRQTLGSLRGLAKAKPEASFQVWNKDSSSKNLIPRLQKIWKNYLSM  119

Query: 117   NKYKVTYKGPGPGVKFSAEALLCHLRDHVNISMIEATDFPFNTSDWEGYLPQEDIRTKAG  176
             NKYKV+YKGPGPG+KFSAEAL CHLRDHVN+SM+E TDFPFNTS+WEGYLP+E IRTKAG
Sbjct: 120   NKYKVSYKGPGPGIKFSAEALRCHLRDHVNVSMVEVTDFPFNTSEWEGYLPKESIRTKAG  179

Query: 177   PWGRCAVVSSAGSLKSSRLGREIDDHDAVLRFNGAPTVKFQQDVGTKTTIRLVNSQLVTT  236
             PWGRCAVVSSAGSLKSS+LGREIDDHDAVLRFNGAPT  FQQDVGTKTTIRL+NSQLVTT
Sbjct: 180   PWGRCAVVSSAGSLKSSQLGREIDDHDAVLRFNGAPTANFQQDVGTKTTIRLMNSQLVTT  239

Query: 237   EAGFLKDSLYNEGILIVWDPSVYHSDIPKWYRNPDYSFFNNFKSYRKLHPDQPFYILKPQ  296
             E  FLKDSLYNEGILIVWDPSVYHSDIPKWY+NPDY+FFNN+K+YRKLHP+QPFYILKPQ
Sbjct: 240   EKRFLKDSLYNEGILIVWDPSVYHSDIPKWYQNPDYNFFNNYKTYRKLHPNQPFYILKPQ  299

Query: 297   MPWELWDIIQEISSELIQPNPPSSGMLGIAIMMSLCDQVDIYEFLPSKRKTDVCYYYQRY  356
             MPWELWDI+QEIS E IQPNPPSSGMLGI IMM+LCDQVDIYEFLPSKRKTDVCYYYQ++
Sbjct: 300   MPWELWDILQEISPEEIQPNPPSSGMLGIIIMMTLCDQVDIYEFLPSKRKTDVCYYYQKF  359

Query: 357   FDSACTMGAYHPLLFEKNMVKHLNLGTDEDIYLLGKATLPGFRTIRC  403
             FDSACTMGAYHPLL+EKN+VKHLN GTDEDIYLLGKATLPGFRTI C
Sbjct: 360   FDSACTMGAYHPLLYEKNLVKHLNQGTDEDIYLLGKATLPGFRTIHC  406
```

FIGURE 1

| Column 1: control | | | Column 2: ST expressing goat | | |
|---|---|---|---|---|---|
| RT | ID | % | RT | ID | % |
| 10.1 | 1354.4 | 7.5% | 10.1 | 1354.4 | 7.1% |
| 10.9 | 1719.6 | 0.8% | 10.9 | 1719.6 | <0.1% |
| 11.7 | 1744.6 | 1.3% | 11.7 | 1744.6 | 0.4% |
| | | | | 1686.6 | 0.7% |
| 12.0 | 1516.4 | 2.5% | 12.0 | 1516.4 | 1.4% |
| 12.5 | 1889.6 | 0.8% | 12.5 | 1889.6 | 2.1% |
| | 1760.4 | 0.8% | | | |
| 13.4 | 1848.6 | 3.7% | 13.4 | 1848.6 | 2.1% |
| | 2035.6 | 0.9% | | 2035.6 | 1.4% |
| 14.0 | 1678.6 | 8.8% | 1.40 | 1678.6 | 6.7% |
| 14.3 | 1994.6 | 1.4% | 14.3 | 1994.6 | 0.5% |
| | 2051.8 | 12.8% | | 2051.8 | 4.1% |
| | | | 14.8 | 2424.8 | 2.8% |
| 15.3 | 2010.6 | 4.0% | 15.3 | 2010.6 | 2.5% |
| | 2197.8 | 4.0% | | 2197.8 | 0.7% |
| | 2067.8 | 2.0% | | 2067.8 | 0.4% |
| | | | 15.8 | 2383.8 | 8.9% |
| 16.1 | 1840.6 | 12.1% | 16.1 | 1840.6 | 11.6% |
| | | | | 2570.6 | 2.9% |
| 16.5 | 2342.8 | 4.2% | 16.5 | 2342.8 | 16.6% |
| | | | | 2529.6 | 1.8% |
| 17.6 | 2002.6 | 27.4% | 17.6 | 2002.6 | 19.3% |
| | 2358.6 | 3.0% | | 2358.6 | 2.4% |
| | | | | 2488.8 | 2.4% |
| 21.2 | 2374.6 | 2.1% | 18.3 | 2346.8 | 1.1% |

FIGURE 5

SEQUENCE LISTING

```
<160> NUMBER OF SEQ ID NOS: 2

<210> SEQ ID NO 1
<211> LENGTH: 402
<212> TYPE: PRT
<213> ORGANISM: Capra hircus

<400> SEQUENCE: 1

Met Thr Arg Thr Ser Leu Lys Lys Phe Phe Ser Cys Cys Val Leu
1               5                   10                  15

Ile Phe Leu Leu Phe Ala Ile Ile Cys Val Trp Lys Glu Lys Lys
                20                  25                  30

Gly Asn Tyr Tyr Glu Phe Leu Lys Leu Gln Asn Lys Glu Tyr Gln Met
                35                  40                  45

Leu Gln Gly Leu Glu Lys Leu Ala Met Ser Ser Ser Gln Pro Gly
    50                  55                  60

Ser Ser Ser Ser Thr His Asn Pro Gln Lys Asn Ile Gln Ala Leu Gly
65                  70                  75                  80

Gly Pro Lys Ala Lys Leu Gly Ala Thr Phe Gln Val Trp Asp Lys Asp
                85                  90                  95

Ser Ser Ser Lys Asn Leu Ala Pro Arg Leu Gln Thr Ile Arg Lys Asn
                100                 105                 110

Tyr Leu Asn Met Asn Lys Tyr Lys Val Thr Tyr Lys Gly Pro Gly Pro
            115                 120                 125

Gly Val Lys Phe Ser Ala Glu Ala Leu Leu Cys His Leu Arg Asp His
    130                 135                 140

Val Asn Ile Ser Met Ile Glu Ala Thr Asp Phe Pro Phe Asn Thr Ser
145                 150                 155                 160

Asp Trp Glu Gly Tyr Leu Pro Gln Glu Asp Ile Arg Thr Lys Ala Gly
                165                 170                 175

Pro Trp Gly Arg Cys Ala Val Val Ser Ser Ala Gly Ser Leu Lys Ser
            180                 185                 190

Ser Arg Leu Gly Arg Glu Ile Asp Asp His Asp Ala Val Leu Arg Phe
        195                 200                 205

Asn Gly Ala Pro Thr Val Lys Phe Gln Gln Asp Val Gly Thr Lys Thr
    210                 215                 220

Thr Ile Arg Leu Val Asn Ser Gln Leu Val Thr Thr Glu Ala Gly Phe
225                 230                 235                 240
```

```
Leu Lys Asp Ser Leu Tyr Asn Glu Gly Ile Leu Ile Val Trp Asp Pro
            245                 250                 255

Ser Val Tyr His Ser Asp Ile Pro Lys Trp Tyr Arg Asn Pro Asp Tyr
                260                 265                 270

Ser Phe Phe Asn Asn Phe Lys Ser Tyr Arg Lys Leu His Pro Asp Gln
            275                 280                 285

Pro Phe Tyr Ile Leu Lys Pro Gln Met Pro Trp Glu Leu Trp Asp Ile
        290                 295                 300

Ile Gln Glu Ile Ser Ser Glu Leu Ile Gln Pro Asn Pro Ser Ser
305                 310                 315                 320

Gly Met Leu Gly Ile Ala Ile Met Met Ser Leu Cys Asp Gln Val Asp
                325                 330                 335

Ile Tyr Glu Phe Leu Pro Ser Lys Arg Lys Thr Asp Val Cys Tyr Tyr
            340                 345                 350

Tyr Gln Arg Tyr Phe Asp Ser Ala Cys Thr Met Gly Ala Tyr His Pro
        355                 360                 365

Leu Leu Phe Glu Lys Asn Met Val Lys Leu Asn Leu Gly Thr Asp Glu
    370                 375                 380

Asp Ile Tyr Leu Leu Gly Lys Ala Thr Leu Pro Gly Phe Arg Thr Ile
385                 390                 395                 400

Arg Cys

<210> SEQ ID NO 2
<211> LENGTH: 406
<212> TYPE: PRT
<213> ORGANISM: Homo sapiens

<400> SEQUENCE: 2

Met Ile His Thr Asn Leu Lys Lys Lys Phe Ser Cys Cys Val Leu Val
1               5                   10                  15

Phe Leu Leu Phe Ala Val Ile Cys Val Trp Lys Glu Lys Lys Lys Gly
            20                  25                  30

Ser Tyr Tyr Asp Ser Phe Lys Leu Gln Thr Lys Glu Phe Gln Val Leu
        35                  40                  45

Lys Ser Leu Gly Lys Leu Ala Met Gly Ser Asp Ser Gln Ser Val Ser
    50                  55                  60

Ser Ser Ser Thr Gln Asp Pro His Arg Gly Arg Gln Thr Leu Gly Ser
65                  70                  75                  80

Leu Arg Gly Leu Ala Lys Ala Lys Pro Glu Ala Ser Phe Gln Val Trp
                85                  90                  95

Asn Lys Asp Ser Ser Ser Lys Asn Leu Ile Pro Arg Leu Gln Lys Ile
            100                 105                 110

Trp Lys Asn Tyr Leu Ser Met Asn Lys Tyr Lys Val Ser Tyr Lys Gly
        115                 120                 125

Pro Gly Pro Gly Ile Lys Phe Ser Ala Glu Ala Leu Arg Cys His Leu
    130                 135                 140

Arg Asp His Val Asn Val Ser Met Val Glu Val Thr Asp Phe Pro Phe
145                 150                 155                 160

Asn Thr Ser Glu Trp Glu Gly Tyr Leu Pro Lys Glu Ser Ile Arg Thr
                165                 170                 175

Lys Ala Gly Pro Trp Gly Arg Cys Ala Val Val Ser Ser Ala Gly Ser
            180                 185                 190

Leu Lys Ser Ser Gln Leu Gly Arg Glu Ile Asp Asp His Asp Ala Val
        195                 200                 205
```

```
Leu Arg Phe Asn Gly Ala Pro Thr Ala Asn Phe Gln Gln Asp Val Gly
    210             215                 220
Thr Lys Thr Thr Ile Arg Leu Met Asn Ser Gln Leu Val Thr Thr Glu
225             230                 235                 240
Lys Arg Phe Leu Lys Asp Ser Leu Tyr Asn Glu Gly Ile Leu Ile Val
            245                 250                 255
Trp Asp Pro Ser Val Tyr His Ser Asp Ile Pro Lys Trp Tyr Gln Asn
        260                 265                 270
Pro Asp Tyr Asn Phe Phe Asn Asn Tyr Lys Thr Tyr Arg Lys Leu His
    275                 280                 285
Pro Asn Gln Pro Phe Tyr Ile Leu Lys Pro Gln Met Pro Trp Glu Leu
    290                 295                 300
Trp Asp Ile Leu Gln Glu Ile Ser Pro Glu Glu Ile Gln Pro Asn Pro
305             310                 315                 320
Pro Ser Ser Gly Met Leu Gly Ile Ile Ile Met Met Thr Leu Cys Asp
            325                 330                 335
Gln Val Asp Ile Tyr Glu Phe Leu Pro Ser Lys Arg Lys Thr Asp Val
            340                 345                 350
Cys Tyr Tyr Tyr Gln Lys Phe Phe Asp Ser Ala Cys Thr Met Gly Ala
        355                 360                 365
Tyr His Pro Leu Leu Tyr Glu Lys Asn Leu Val Lys His Leu Asn Gln
    370                 375                 380
Gly Thr Asp Glu Asp Ile Tyr Leu Leu Gly Lys Ala Thr Leu Pro Gly
385             390                 395                 400
Phe Arg Thr Ile His Cys
            405
```

PROTEINS WITH MODIFIED GLYCOSYLATION AND METHODS OF PRODUCTION THEREOF

RELATED APPLICATIONS

This application is a national stage filing under 35 U.S.C. § 371 of International Application No. PCT/IB2014/001236, entitled "Proteins with Modified Glycosylation and Methods of Production Thereof," filed Feb. 13, 2014, which was published under PCT Article 21(2) in English and which claims the benefit under 35 U.S.C. § 119(e) of U.S. Provisional Application Ser. No. 61/764,502, entitled "Proteins with Modified Glycosylation and Methods of Production Thereof," filed on Feb. 13, 2013, the entire contents of each of which is incorporated by reference herein in its entirety.

FIELD OF THE INVENTION

The disclosure relates to the field of proteins and methods of protein production.

BACKGROUND OF THE INVENTION

Transgenic production of proteins in the mammary gland allows for the production of large amounts of proteins, including therapeutic proteins. However, the glycosylation pattern of proteins produced in the mammary gland sometimes differs from the glycosylation pattern of serum produced proteins. Methods to modify the glycosylation of mammary gland produced proteins are needed therefore.

SUMMARY OF THE INVENTION

In one aspect, the disclosure provides proteins with modified glycosylation and methods of their production. In aspect, the disclosure provides transgenic animals and cells for the production of proteins with modified glycosylation. In some embodiment, the modified glycosylation is increased sialylation.

In one aspect, the disclosure provides a method of producing protein with modified glycosylation, the method comprising providing a transgenic mammal that has been modified to have increased expression of sialyl transferase in the mammary gland, wherein the transgenic mammal expresses a protein in the mammary gland, and harvesting the protein from the mammary gland of the transgenic mammal.

In one aspect, the disclosure provides a method of producing protein with modified glycosylation, the method comprising providing a mammary epithelial cell that has been modified to have increased expression of sialyl transferase, wherein the mammary epithelial cell expresses a protein, and harvesting the protein from the mammary epithelial cells.

In some embodiments of the methods provided herein, the glycosylation is modified compared to a protein produced in a transgenic mammal or mammary epithelial cell that has not been modified to have increased expression of sialyl transferase. In some embodiments of the methods provided herein, the modified glycosylation is increased sialylation.

In one aspect, the disclosure provides a method of producing protein with increased sialylation, the method comprising providing a transgenic mammal that has been modified to have increased expression of sialyl transferase in the mammary gland, wherein the transgenic mammal expresses a protein in the mammary gland, and harvesting the protein with increased sialylation from the mammary gland of the transgenic mammal.

In some embodiments of the methods provided herein, the sialylation is increased compared to a protein produced in a transgenic mammal or mammary epithelial cell that has not been modified to have increased expression of sialyl transferase.

In some embodiments of the methods provided herein, the protein with modified glycosylation or protein with increased sialylation is a human protein. In some embodiments of the methods provided herein, the protein with modified glycosylation or protein with increased sialylation is an antibody. In some embodiments of the methods provided herein, the protein with modified glycosylation or protein with increased sialylation is antithrombin. In some embodiments of the methods provided herein, the protein with modified glycosylation or protein with increased sialylation is alpha-1 antitrypsin.

In one aspect, the disclosure provides a protein with modified glycosylation or protein with increased sialylation produced according to any of the methods provided herein.

In one aspect, the disclosure provides a composition comprising the protein with modified glycosylation or protein with increased sialylation produced according to any of the methods provided herein, the composition further comprising milk.

In one aspect, the disclosure provides a method of increasing the sialyl transferase activity in the mammary gland, the method comprising providing a transgenic mammal that has been modified to have increased expression of sialyl transferase in the mammary gland.

In one aspect, the disclosure provides a method of producing sialyl transferase, the method comprising providing a transgenic mammal that has been modified to have increased expression of sialyl transferase in the mammary gland, and harvesting the sialyl transferase from the mammary gland of the transgenic mammal. In some embodiments of the methods provided herein, the method further comprises using the sialyl transferase to sialylate a protein.

In one aspect, the disclosure provides a method of increasing the sialyl transferase activity in the mammary gland, the method comprising producing a transgenic mammal that has been modified to have increased expression of sialyl transferase in the mammary gland. In one aspect, the disclosure provides a method of producing sialyl transferase, the method comprising producing a transgenic mammal that has been modified to have increased expression of sialyl transferase in the mammary gland, and harvesting the sialyl transferase from the mammary gland of the transgenic mammal. In some embodiments of the methods provided herein, the method further comprises using the sialyl transferase to sialylate a protein. In some embodiments the sialyl transferase is placed in contact with the protein.

In one aspect, the disclosure provides a sialyl transferase produced according to any of the methods provided herein.

In one aspect, the disclosure provides a composition comprising the sialyl transferase produced according to any of the methods provided herein and further comprising milk.

In some embodiments of the methods, proteins, compositions, transgenic mammals or mammary gland epithelial cells provided herein, the transgenic mammal or mammary gland epithelial cell has been modified by introducing into the genome of the transgenic mammal or mammary gland epithelial cell a nucleic acid sequence encoding a sialyl transferase.

In some embodiments of the methods, proteins, compositions, transgenic mammals or mammary gland epithelial cells provided herein, the protein expressed in the transgenic mammal or mammary gland epithelial cell is encoded by a nucleic acid sequence introduced into the genome of the transgenic mammal or mammary gland epithelial cell.

In one aspect, the disclosure provides a transgenic mammal that has been modified to have increased expression of sialyl transferase in the mammary gland. In some embodiments of transgenic mammals provided herein, the transgenic mammal further expresses an exogenous protein in the mammary gland. In some embodiments of transgenic mammals provided herein, the exogenous protein is a human protein. In some embodiments of transgenic mammals provided herein, the exogenous protein is an antibody. In some embodiments of transgenic mammals provided herein, the exogenous protein is antithrombin. In some embodiments of transgenic mammals provided herein, the exogenous protein is alpha-1 antitrypsin.

In one aspect, the disclosure provides a mammary epithelial cell that has been modified to have increased expression of sialyl transferase. In some embodiments of the mammary epithelial cells provided herein, the mammary epithelial cell further expresses an exogenous protein. In some embodiments of the mammary epithelial cells provided herein, the exogenous protein is a human protein. In some embodiments of the mammary epithelial cells provided herein, the exogenous protein is an antibody. In some embodiments of the mammary epithelial cells provided herein, the exogenous protein is antithrombin. In some embodiments of the mammary epithelial cells provided herein, the exogenous protein is alpha-1 antitrypsin.

In some embodiments of the methods, proteins, compositions, transgenic mammals or mammary gland epithelial cells provided herein, the transgenic mammal is an ungulate. In some embodiments, the ungulate is a goat.

In some embodiments of the methods, proteins, compositions, transgenic mammals or mammary gland epithelial cells provided herein, the expression of sialyl transferase is under the control of a milk promoter. In some embodiments, the milk promoter is a goat beta casein promoter.

In some embodiments of the methods, proteins, compositions, transgenic mammals or mammary gland epithelial cells provided herein, the sialyl transferase is beta-galactosamide alpha-2,6-sialyltranferase.

In some embodiments of the methods, proteins, compositions, transgenic mammals or mammary gland epithelial cells provided herein, the sialyl transferase is beta-galactosamide alpha-2,3-sialyltranferase.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the Figures. The invention is capable of other embodiments and of being practiced or of being carried out in various ways. Also, the phraseology and terminology used herein is for the purpose of description and should not be regarded as limiting.

BRIEF DESCRIPTION OF THE DRAWINGS

The figures are illustrative only and are not required for enablement of the disclosure.

FIG. 1 shows the sequence of ST6 beta-galactosamide alpha-2,6-sialyltranferase GENE ID: 100861310 ST6GAL1 [Capra hircus] (SEQ ID NO:1), top sequence labeled "Query", as compared to the human protein (SEQ ID NO:2), bottom sequence labeled "Subject".

FIG. 3 provides isoelectric focusing (IEF) gels showing proteins with increased levels of sialic acid.

FIG. 5 shows the sialylation of lactoferrin in a transgenic goat that overexpresses sialyl transferase in the mammary gland (column 2) and a control animal (column 1).

DETAILED DESCRIPTION OF THE INVENTION

Figure 2:
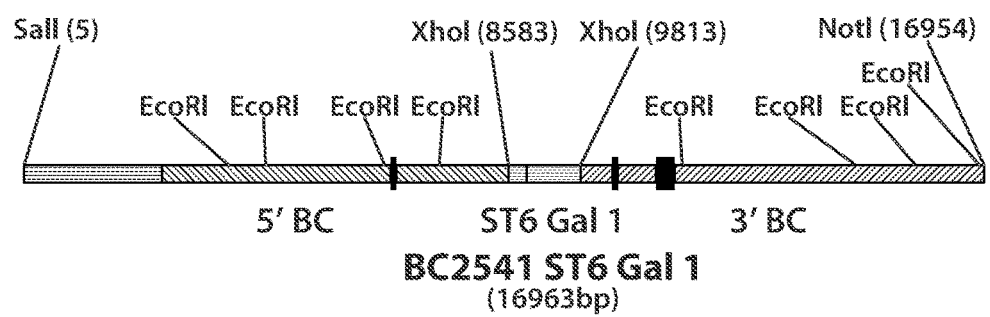
FIG. 2 provides a schematic representation of the ST6 beta-galactosamide alpha-2,6-sialyltransferase gene.

In one aspect, the disclosure provides proteins with modified glycosylation and methods of production thereof. In one aspect, the disclosure provides transgenic mammals and cells for the production of proteins with modified glycosylation.

In one aspect, the disclosure provides proteins with increased sialylation and methods of production thereof. In one aspect, the disclosure provides transgenic mammals and cells for the production of proteins with increased sialylation. In one aspect, the disclosure provides transgenic mammals and cells for the production of proteins with increased sialylation, wherein the transgenic mammal or cell has been modified to have increased expression of sialyl transferase.

Production of protein in the mammary gland of transgenic non-human mammals has the advantage of allowing for the production of large amounts of protein. A variety of proteins can be produced in the mammary gland and transgenic production in non-human mammals has been used to produce human therapeutic proteins, such as serum proteins. An example of a transgenically produced serum protein is Atryn®, a transgenically produced antithrombin, which has been approved for use in both the US and Europe (See e.g., U.S. Pat. Nos. 5,843,705, 6,441,145, 7,019,193 and 7,928,064).

Proteins that are transgenically produced in the mammary gland have the same amino acid sequence as "natural" proteins, as long as the nucleic acid encoding the protein that is introduced into the transgenic mammal is the same as the "natural" protein. However, if the transgenic protein is a glycoprotein, there may be differences in the glycosylation pattern of proteins produced in the mammary gland of transgenic non-human mammals as compared to "natural" proteins. For instance, mammary gland produced proteins can have a lower level of sialylation compared to the same protein isolated from serum (See e.g., Edmunds, T, et al., Blood 91(12), 1998, 4561-4571; Geun-Cheol Gil et al., Glycobiology 18(7), 2008, 526-539). Differences in glycosylation between recombinantly produced proteins and natural proteins are not unique to the production of recombinant (transgenic) protein in the mammary gland. Almost any production method of a recombinant protein e.g., production in CHO cells, can result in a difference in glycosylation as compared to natural proteins, merely because of different availability and activity of glycosylation enzymes between cell types. A difference in glycosylation of the recombinantly produced protein may or may not be relevant. Recombinant glycoproteins, even therapeutic proteins, can still have the desired biological properties even if the glycosylation is different from the natural protein. In some instances, however, a difference in glycosylation may be preferred because the different glycosylation may provide the recombinantly produced proteins different functional properties as compared to the natural protein (e.g., a slower clearing rate).

However, in some instances it is desirable that the glycosylation pattern of a recombinantly produced protein resemble, or be identical to, the glycosylation pattern of a natural protein (e.g., a protein found in the blood stream).

A variety of methods are available to modify the glycosylation of recombinantly produced proteins. For instance, inhibitors of specific glycosylation enzymes can be added to the cells that are producing proteins resulting in a modified glycosylation of the produced proteins. In addition, glycosylated proteins can be modified post-production, for instance by incubating the protein with one or more glycosylation enzymes and/or modifying the glycosylation through chemical reactions.

In one aspect, the disclosure provides methods of producing proteins with modified glycosylation. In one aspect, the disclosure provides transgenic mammals for the production of proteins with modified glycosylation. In some embodiments, the transgenic mammals allow for the production of proteins with modified glycosylation in the mammary gland.

In one aspect, the disclosure provides methods of producing proteins with modified glycosylation. In one aspect, the disclosure provides cells for the production of proteins with modified glycosylation. In some embodiments, the cells are mammary epithelial cells.

In one aspect, the disclosure provides proteins with modified glycosylation. In some embodiments the proteins are human proteins.

In one aspect, the disclosure provides a method of producing protein with modified glycosylation comprising providing or producing a transgenic mammal that has been/is modified to have increased expression of sialyl transferase in the mammary gland, wherein the transgenic mammal expresses a protein in the mammary gland, and harvesting the protein from the mammary gland of the transgenic mammal. In some embodiments, the glycosylation is modified compared to a protein produced in a transgenic mammal or mammary epithelial cell that has not been modified to have increased expression of sialyl transferase. In some embodiments, the modified glycosylation is increased sialylation.

In one aspect, the disclosure provides a method of producing protein with modified glycosylation comprising providing or producing a mammary epithelial cell that has been/is modified to have increased expression of sialyl transferase, wherein the mammary epithelial cell expresses a protein, and harvesting the protein from the mammary epithelial cells. In some embodiments, the glycosylation is modified compared to a protein produced in a transgenic mammal or mammary epithelial cell that has not been modified to have increased expression of sialyl transferase. In some embodiments, the modified glycosylation is increased sialylation.

In one aspect, the disclosure provides a method of producing protein with increased sialylation, the method comprising providing a transgenic mammal that has been modified to have increased expression of sialyl transferase in the mammary gland, wherein the transgenic mammal expresses a protein in the mammary gland, and harvesting the protein with increased sialylation from the mammary gland of the transgenic mammal. In some embodiments, the sialylation is increased compared to a protein produced in a transgenic mammal or mammary epithelial cell that has not been modified to have increased expression of sialyl transferase.

A protein with modified glycosylation, as used herein, refers to a protein having a glycosylation pattern resulting from production in the mammary gland of a transgenic mammal or mammary epithelial cells wherein the mammary gland or mammary epithelial cells has an increased expression of sialyl transferase(s). The glycosylation is modified compared to the same protein produced in the mammary gland of a transgenic mammal or mammary epithelial cell that does not have increased expression of sialyl transferase(s). In some embodiments, the modified glycosylation is increased sialylation (i.e., an increased number of sialic acid groups on the oligomannose chains). In some embodiments, the sialylation of the protein is increased by 10%, by 20%, by 30%, by 40%, by 50%, by 60%, by 70%, by 80%, by 90%, or by 100% or more, compared to the same protein produced in the mammary gland of a transgenic mammal or mammary epithelial cell that does not have increased expression of sialyl transferases. Sialylation levels can be determined for instance by analyzing the glycosylation of the protein with HPLC/MS.

It should be appreciated that the level of sialylation is increased compared to the same protein produced in the mammary gland of a transgenic mammal or mammary epithelial cell that does not have increased expression of sialyl transferases. Proteins with increased sialylation, as defined herein, may still have lower levels of sialylation compared to "natural proteins" (e.g., proteins produced in the liver). In some embodiments, the proteins with increased sialylation have a level of sialylation that is at least 10%, at least 20%, at least 30%, at least 40%, at least 50%, at least 60%, at least 70%, at least 80%, at least 90%, at least 100%, at least 200% or at least 300% or more, compared to the sialylation level in a "natural protein". As shown herein, the expression levels of sialyl transferases in the mammary gland and mammary epithelial cell is lower than the expression level in other organs and cells (e.g., the liver). Accordingly, glycoproteins produced in mammary gland or mammary epithelial cell generally will have a lower level of sialylation than the same protein produced in other organs and cells (e.g., the liver). This level may be lower even if the mammary gland or mammary epithelial cell has been modified to have increased expression of sialyl transferase according to the methods provided herein.

It should further be appreciated that production of a protein in the mammary gland of a transgenic mammal or mammary epithelial cell with increased expression of sialyl transferases may result in modified glycosylation that is not limited to increased sialylation. For instance, the increased availability of sialyl transferase may lead to oligosaccharide chains that are shorter because they are capped with sialic acid preventing further addition of monosaccharides. In addition, for instance, the increased availability of sialyl transferases may lead to a different availability of substrates for glycosylation leading to the synthesis of oligosaccharide side chains with a different monosaccharide pattern.

It is envisioned that a variety of proteins with modified glycosylation (e.g., increased sialylation) can be produced according to the methods provided herein. In some embodiments the protein is an exogenous protein (i.e., a protein not naturally found in the genome of the transgenic mammal or mammary epithelial cell, such as a human protein in a transgenic goat). In some embodiments, the protein with modified glycosylation is a human protein. Proteins with modified glycosylation that can be produced according to the methods provided herein include antibodies and glycoproteins that are active in blood homeostasis, such as anti-thrombin and alpha-antitrypsin. In some embodiments, the protein "to be modified" is a transgenic protein that is expressed in the mammary gland of the transgenic mammal or mammary gland epithelial cell because it is encoded by a nucleic acid sequence introduced into the genome of the transgenic mammal or mammary gland epithelial cell. However, in some embodiments, the proteins with modified glycosylation that are produced according to the methods provided herein are proteins that are naturally expressed in the mammary gland or mammary epithelial cells, such as lactoferrin.

In one aspect, the disclosure provides a method of increasing the sialyl transferase activity in the mammary gland comprising providing a transgenic mammal that has been modified to have increased expression of sialyl transferase in the mammary gland. In one aspect, the disclosure provides a method of increasing the sialyl transferase activity in mammary epithelial cells comprising providing or producing a mammary epithelial cell that has been/is modified to have increased expression of sialyl transferase. Increased expression, as used herein, refers to an increase in expression compared to an unmodified ("natural") mammary gland or unmodified mammary epithelial cell. It should be appreciated, and also shown herein, that an unmodified mammary gland or unmodified mammary epithelial cell has some residual expression of sialyl transferase. Thus, in some embodiments, the increased expression of sialyl transferase in the mammary gland or mammary epithelial cells is 2× higher or more, 3× higher or more, 4× higher or more, 5× higher or more, 10× higher or more, 20× higher or more, 50× higher or more, 100× higher or more, or 1000× higher or more than the natural expression of sialyl transferase in the mammary gland or mammary epithelial cells.

The mammary gland or mammary epithelial cells can be modified in a variety of ways to increase expression of sialyl transferase. In some embodiments, the expression is increased by upregulating the expression of one or more sialyl transferases that are naturally present in the genome. In some embodiments, the expression is increased by introducing a new mammary specific promoter into the genome upstream of the one or more sialyl transferases that are naturally present in the genome. In some embodiments, the transgenic mammal or mammary gland epithelial cell has been modified by introducing into the genome of the transgenic mammal or mammary gland epithelial cell a nucleic acid sequence encoding a sialyl transferase. It should be appreciated that the transgenic mammals and mammary epithelial cells that have been modified to express sialyl transferase may also express a protein to be modified (e.g., an exogenous protein).

Sialyl transferases are members of the glycosyltransferases group of enzymes. Sialyl transferase is an enzyme that can transfer sialic acid onto an oligosaccharide, including oligosaccharides found on glycosylated proteins. In general sialyl transferases introduced sialic acids on the terminal positions of glycoconjugate sugar chains. Sialyl transferases are categorized according to their specific activity, and are generally classified in three groups: alpha-2,6-sialytransferases, alpha-2,3-sialytransferases and alpha-2,8-sialytransferases, which can introduce sialic acid groups through an alpha-2,6-, alpha-2,3-, and alpha-2,8-linkage, respectively (See e.g., Harduin-Lepers et al., The human sialyltransferase family, Biochimie 83: 727-737, 2001).

The alpha-2,6-sialytransferases are further classified in sialyl transferases that attach a sialic acid to galactose ("ST6Gal I", "beta-galactosamide alpha-2,6-sialyltransferase" or ST6 beta-galactosamide alpha-2,6-sialyltransferase 1"), and sialyl transferases that attach a sialic acid to GalNAc ("ST6GalNAc I-VI"). The beta-galactosamide alpha-2,6-sialyltransferase mediates the transfer of a sialic acid residue to a terminal Gal residue on a disaccharide found as a free disaccharide or found as a terminal unit on a N-linked or O-linked oligosaccharide. Thus, in some embodiments, the disclosure provides methods and compositions that allow for N-linked sialylation. In some embodiments, the disclosure provides methods and compositions that allow for O-linked sialylation.

The GalNAc alpha-2,6-sialyltransferases can attach sialic acid to non-terminal GalNAc residues.

The alpha-2,3 sialyltransferases mediate the transfer of sialic acid though a 2,3 linkage to a terminal Gal residue on glycolipids and glycoproteins.

The alpha-2,8 sialyltransferases generally are involved in the generation of poly-sialic acid chains.

In some embodiments, the sialyl transferase is beta-galactosamide alpha-2,6-sialyltransferase ("ST6 Gal"), alpha-N-acetylgalactosaminide alpha-2,6-sialyltransferase, beta-galactoside alpha-2,3-sialyltransferase, N-acetyllactosaminide alpha-2,3-sialyltransferase, alpha-N-acetylneuraminide alpha-2,8-sialyltransferase, or lactosylceramide alpha-2,3-sialyltransferase. In some embodiments the sialyl transferase is beta-galactosamide alpha-2,6-sialyltransferase ("ST6 Gal"). In some embodiments, the sialyl transferase is beta-galactoside alpha-2,3-sialyltransferase. Sequences of human sialyl transferases are provided, for instance, in Harduin-Lepers et al., (The human sialyltransferase family, Biochimie 83: 727-737, 2001)

In general the species of sialyl transferase used according to the methods of the invention will be the same as species of transgenic mammal or the mammary epithelial cell. For instance, goat sialyl transferase is introduced in a transgenic goat or goat mammary epithelial cells. However, it should be appreciated that the sialyl transferase used may also be from a different species as the transgenic mammal or the mammary epithelial. In some embodiments, the sialyl transferase introduced into the transgenic mammal or the mammary epithelial cell is from the same species as the protein to be modified (e.g., a human sialyl transferase is used to generate a human antibody with increased sialylation). In some embodiments, the transgenic mammal or the mammary epithelial cell transgenically expresses a sialyl transferase and an exogenous protein, from the same species (e.g., a goat is transgenic for both human sialyl transferase and a human therapeutic antibody).

In one aspect, the disclosure provides methods and compositions to treat inflammation. It has been shown that the anti-inflammatory activity of intravenously administered Ig results from a subset of the IgG molecules that have terminal alpha-2,6-sialic acid linkages on their Fc-linked glycans. The anti-inflammatory activity of the population of the intravenously administered Ig was increased by introducing a terminal alpha-2,6-sialic acid linkage on all Fc-linked glycans (See e.g., Anthony et al., Identification of a receptor required for the anti-inflammatory activity of IVIG, PNAS 105: 19571-19578, 2008). The methods provided herein allow for the production in the mammary gland of transgenic animals and mammary epithelial cells of exogenous proteins, such as therapeutic antibodies, with increased levels of alpha-2,6-sialylation. Thus, the methods provided herein allow for the production in the mammary gland of transgenic animals and mammary epithelial cells of exogenous proteins, such as therapeutic antibodies, with increased anti-inflammatory properties.

It should be appreciated that the methods provided herein to increase the anti-inflammatory properties of therapeutic antibodies can be applied to any therapeutic antibody. Thus, in some embodiments, the disclosure provides therapeutic antibodies with increased anti-inflammatory activity. It should further be appreciated that the methods provided for the generation of antibodies with increased anti-inflammatory activity may be applied to anti-inflammatory antibodies, thereby providing anti-inflammatory antibodies with synergistic mode of actions (through binding to an anti-inflammatory target and through the alpha-2,6-sialic acid linkages on their Fc-linked glycans). Therapeutic antibodies for anti-inflammatory treatment include anti-TNF alpha antibodies such as infliximab/Remicade (Centocor) a mouse-human chimeric monoclonal anti TNF-antibody, adalimumab/Humira (Abbott) a fully human anti-TNF antibody, and golimumab/Simponi (Centocor) a fully human anti-TNF antibody, therapeutic TNF-alpha binders that are antibody-based including Etanercept/Enbrel (Amgen) a fusion protein of the extracellular domain of TNF-receptor fused to the Fc region of Ig1, and certolizumab pegol/Cimzia (UCB) a Pegylated Fab' fragment of humanized monoclonal anti-TNF antibody. Therapeutic antibodies for anti-inflammatory treatment also include non-TNF-alpha anti-cytokine antibodies such as anti-IL5 (e.g., mepolizumab), anti-IL2 (e.g., daclizumab), anti-IL4 and anti-IL13 antibodies. Therapeutic antibodies for anti-inflammatory treatment also include anti-IgE antibodies (e.g., omalizumab), anti-CD62 antibodies, and others.

Thus, in one aspect, the disclosure provides transgenic animals (and mammary epithelial cells) that are transgenic for the production in the mammary gland of an exogenous therapeutic antibody and that are transgenic for the production of sialyl transferase. The therapeutic antibodies produced by such animals and cells have increased levels of terminal alpha-2,6-sialic acid linkages on their Fc-linked glycans, and thereby have increased anti-inflammatory activity (as compared to therapeutic antibodies produced in transgenic animals and mammary cells that are not transgenic for the expression of sialyl transferase). In some embodiments, the transgenic animals (and mammary epithelial cells) are transgenic for the production in the mammary gland of an exogenous anti-inflammatory antibody and are transgenic for the production of sialyl transferase. In some embodiments, the anti-inflammatory antibody is an anti-TNF-alpha antibody. In some embodiments, the anti-inflammatory antibody is adalimumab.

In one aspect, the disclosure provides methods of treating inflammation in a subject comprising administering to a subject the antibodies with increased anti-inflammatory properties provided herein.

In one aspect, the disclosure provides a method of producing sialyl transferase comprising providing or producing a transgenic mammal that has been/is modified to have increased expression of sialyl transferase in the mammary gland, and harvesting the sialyl transferase from the mammary gland of the transgenic mammal. In some embodiments, the transgenic mammal or mammary gland epithelial cell has been modified by introducing into the genome of the transgenic mammal or mammary gland epithelial cell a nucleic acid sequence encoding a sialyl transferase.

In some embodiments, the sialyl transferase produced according to the methods provided herein is used to sialylate a protein.

In one aspect, the disclosure provides a sialyl transferase produced by providing a transgenic mammal that has been modified to have increased expression of sialyl transferase in the mammary gland, and harvesting the sialyl transferase from the mammary gland of the transgenic mammal. In some embodiments, the transgenic mammal has been modified by introducing into the genome of the transgenic mammal a nucleic acid sequence encoding a sialyl transferase.

In some embodiments, the sialyl transferase is in a composition that further comprises milk.

In one aspect, the disclosure provides a protein with modified glycosylation produced by providing or producing a transgenic mammal that has been/is modified to have increased expression of sialyl transferase in the mammary gland, wherein the transgenic mammal expresses the protein in the mammary gland and harvesting the protein with modified glycosylation from the mammary gland of the transgenic mammal. In some embodiments, the transgenic mammal has been modified by introducing into the genome of the transgenic mammal cell a nucleic acid sequence encoding a sialyl transferase.

In some embodiments, the protein with modified glycosylation is in a composition that further comprises milk. In some embodiments, the protein with modified glycosylation is a human protein. In some embodiments, the protein with modified glycosylation is an antibody, antithrombin or alpha antitrypsin.

Transgenic Mammals

In one aspect, the disclosure provides a transgenic mammal that has been modified to have increased expression of sialyl transferase in the mammary gland. In some embodiments, the transgenic mammal is an ungulate. In some embodiments, the ungulate is a goat.

In one aspect, the disclosure provides a mammary epithelial cell that has been modified to have increased expression of sialyl transferase.

In some embodiments, the transgenic mammal or mammary gland epithelial cell has been modified by introducing into the genome of the transgenic mammal or mammary gland epithelial cell a nucleic acid sequence encoding a sialyl transferase. In some embodiments, the expression of sialyl transferase is under the control of a milk promoter. In some embodiments, the milk promoter is a goat beta casein promoter.

In one aspect, the disclosure provides methods of producing proteins with modified glycosylation, wherein the protein to be modified is expressed in the mammary gland or mammary epithelial cells. In some embodiments, the protein expressed in the transgenic mammal or mammary gland epithelial cell is encoded by a nucleic acid sequence introduced into the genome of the transgenic mammal or mammary gland epithelial cell. In some embodiments, the expression of sialyl transferase is under the control of a milk promoter. In some embodiments, the milk promoter is a goat beta casein promoter.

In one aspect, the disclosure provides a transgenic non-human mammal that has increased expression of sialyl transferase in the mammary gland. In some embodiments, the transgenic non-human mammal that has increased expression of sialyl transferase in the mammary gland also expresses a transgenic protein in the mammary gland (e.g., an exogenous protein).

In one aspect, the disclosure provides mammary gland epithelial cells that have increased expression of sialyl transferase. In some embodiments, the mammary gland epithelial cells that have increased expression of sialyl transferase also express a recombinant protein (e.g., an exogenous protein).

In one aspect, the disclosure provides a method of production of sialyl transferase comprising expressing in the milk of a transgenic non-human mammal having a sialyl transferase encoded by a nucleic acid construct. In one aspect, the disclosure provides a method of the production of a protein with modified glycosylation comprising expressing in the milk of a transgenic non-human mammal that has increased expression of sialyl transferase in the mammary gland and a transgenic protein (e.g., an exogenous protein) encoded by a nucleic acid construct.

In some embodiments, the method of producing the sialyl transferase or protein with modified glycosylation comprises:
  (a) transfecting non-human mammalian cells with a transgene DNA construct encoding sialyl transferase and/or the protein to be modified;
  (b) selecting cells in which said transgene DNA construct(s) has/have been inserted into the genome of the cells; and
  (c) performing a first nuclear transfer procedure to generate a non-human transgenic mammal heterozygous for sialyl transferase and/or protein to be modified and that can express the sialyl transferase and or protein with modified glycosylation in its milk, and, optionally
  (d) repeating one or more of the steps to create a transgenic mammal that can express both the sialyl transferase and protein to be modified in the mammary gland. In one aspect, the disclosure provides a method of:
  (a) providing a non-human transgenic mammal engineered to express sialyl transferase and protein to be modified (e.g., an exogenous protein).
  (b) expressing sialyl transferase and protein to be modified in the milk of the non-human transgenic mammal; and
  (c) isolating the protein with modified glycosylation produced in the milk.

Transgenic mammals can also be generated according to methods known in the art (See e.g., U.S. Pat. No. 5,945,577). Mammals suitable for transgenic expression, include, but are not limited to goat, sheep, bison, camel, cow, pig, rabbit, buffalo, horse, rat, mouse or llama. Suitable mammals also include bovine, caprine, ovine and porcine, which relate to various species of cows, goats, sheep and pigs (or swine), respectively. Suitable mammals also include ungulates. As used herein, "ungulate" is of or relating to a hoofed typically herbivorous quadruped mammal, including, without limitation, sheep, swine, goats, cattle and horses. In one embodiment, the mammals are generated by co-transfecting primary cells with separate constructs. These cells are then used for nuclear transfer. Alternatively, if micro-injection is used to generate the transgenic mammals, the constructs may be injected.

Mammals that are transgenic for one protein (e.g., sialyl transferase) may be crossed with mammals that are transgenic for the protein to be modified, thereby generating mammals that are transgenic both for sialyl transferase and for the protein to be modified.

Cloning will result in a multiplicity of transgenic mammals—each capable of producing a sialyl transferase or other gene construct of interest. The production methods include the use of the cloned mammals and the offspring of those mammals. In some embodiments, the cloned mammals are caprines, bovines or mice. Cloning also encompasses the nuclear transfer of fetuses, nuclear transfer, tissue and organ transplantation and the creation of chimeric offspring.

One step of the cloning process comprises transferring the genome of a cell that contains the transgene encoding the sialyl transferase and/or protein to be modified into an enucleated oocyte. As used herein, "transgene" refers to any piece of a nucleic acid molecule that is inserted by artifice into a cell, or an ancestor thereof, and becomes part of the genome of a mammal which develops from that cell. Such a transgene may include a gene which is partly or entirely exogenous (i.e., foreign) to the transgenic mammal, or may represent a gene having identity to an endogenous gene of the mammal.

Suitable mammalian sources for oocytes include goats, sheep, cows, pigs, rabbits, guinea pigs, mice, hamsters, rats, non-human primates, etc. Preferably, oocytes are obtained from ungulates, and most preferably goats or cattle. Methods for isolation of oocytes are well known in the art. Essentially, the process comprises isolating oocytes from the ovaries or reproductive tract of a mammal, e.g., a goat. A readily available source of ungulate oocytes is from hormonally-induced female mammals. For the successful use of techniques such as genetic engineering, nuclear transfer and cloning, oocytes may preferably be matured in vivo before these cells may be used as recipient cells for nuclear transfer, and before they were fertilized by the sperm cell to develop into an embryo. Metaphase II stage oocytes, which have been matured in vivo, have been successfully used in nuclear transfer techniques. Essentially, mature metaphase II oocytes are collected surgically from either non-super ovulated or super ovulated mammals several hours past the onset of estrus or past the injection of human chorionic gonadotropin (hCG) or similar hormone.

One of the tools used to predict the quantity and quality of the recombinant protein expressed in the mammary gland is through the induction of lactation (Ebert K M, 1994). Induced lactation allows for the expression and analysis of protein from the early stage of transgenic production rather than from the first natural lactation resulting from pregnancy, which is at least a year later. Induction of lactation can be done either hormonally or manually.

In some embodiments, the compositions of sialyl transferase and/or protein with modified glycosylation produced according to the methods provided herein further comprise milk.

In some embodiments the methods provided herein include a step of harvesting (e.g., isolating) the sialyl transferase and/or protein with modified glycosylation from the milk of a transgenic mammal (See e.g., Pollock et al., Journal of Immunological Methods, Volume 231, Issues 1-2, 10 Dec. 1999, Pages 147-157).

Constructs for the Generation of Transgenic Mammals

In some embodiments, to produce primary cell lines containing a construct (e.g., encoding sialyl transferase and/or protein to be modified) for use in producing transgenic mammals (e.g., goats) by nuclear transfer, the constructs can be transfected into primary (goat) skin epithelial cells, which are clonally expanded and fully characterized to assess transgene copy number, transgene structural integrity and chromosomal integration site. As used herein, "nuclear transfer" refers to a method of cloning wherein the nucleus from a donor cell is transplanted into an enucleated oocyte.

Coding sequences for proteins of interest (e.g., sialyl transferase) can be obtained by screening libraries of genomic material or reverse-transcribed messenger RNA derived from the mammal of choice (such as an ungulate, rodent, etc.), obtained from sequence databases such as NCBI, Genbank, or by obtaining the sequences of sialyl transferase and/or protein to be modified, etc. The sequences can be cloned into an appropriate plasmid vector and amplified in a suitable host organism, like $E.$ $coli$. After amplification of the vector, the DNA construct can be excised, purified from the remains of the vector and introduced into expression vectors that can be used to produce transgenic mammals. The transgenic mammals will have the desired transgenic protein integrated into their genome.

After amplification of the vector, the DNA construct can be excised with the appropriate 5' and 3' control sequences, purified away from the remains of the vector and used to produce transgenic mammals that have integrated into their genome the desired non-glycosylated related transgenic protein. Conversely, with some vectors, such as yeast artificial chromosomes (YACs), it is not necessary to remove the assembled construct from the vector; in such cases the amplified vector may be used directly to make transgenic mammals. The coding sequence can be operatively linked to a control sequence, which enables the coding sequence to be expressed in the milk of a transgenic non-human mammal.

A DNA sequence which is suitable for directing production of sialyl transferase and/or protein to be modified to the milk of transgenic mammals can carry a 5'-promoter region derived from a naturally-derived milk protein. This promoter is consequently under the control of hormonal and tissue-specific factors and is most active in lactating mammary tissue. In some embodiments, the promoter is a caprine beta casein promoter. The promoter can be operably linked to a DNA sequence directing the production of a protein leader sequence, which directs the secretion of the transgenic protein across the mammary epithelium into the milk. In some embodiments, a 3'-sequence, which can be derived from a naturally secreted milk protein, can be added to improve stability of mRNA.

As used herein, a "leader sequence" or "signal sequence" is a nucleic acid sequence that encodes a protein secretory signal, and, when operably linked to a downstream nucleic acid molecule encoding a transgenic protein directs secretion. The leader sequence may be the native human leader sequence, an artificially-derived leader, or may obtained from the same gene as the promoter used to direct transcription of the transgene coding sequence, or from another protein that is normally secreted from a cell, such as a mammalian mammary epithelial cell.

In some embodiments, the promoters are milk-specific promoters. As used herein, a "milk-specific promoter" is a promoter that naturally directs expression of a gene in a cell that secretes a protein into milk (e.g., a mammary epithelial cell) and includes, for example, the casein promoters, e.g., α-casein promoter (e.g., alpha S-1 casein promoter and alpha S2-casein promoter), β-casein promoter (e.g., the goat beta casein gene promoter (DiTullio, BIOTECHNOLOGY 10:74-77, 1992), γ-casein promoter, κ-casein promoter, whey acidic protein (WAP) promoter (Gordon et al., BIO-TECHNOLOGY 5: 1183-1187, 1987), β-lactoglobulin promoter (Clark et al., BIOTECHNOLOGY 7: 487-492, 1989) and α-lactalbumin promoter (Soulier et al., FEBS LETTS. 297:13, 1992). Also included in this definition are promoters that are specifically activated in mammary tissue, such as, for example, the long terminal repeat (LTR) promoter of the mouse mammary tumor virus (MMTV).

As used herein, a coding sequence and regulatory sequences are said to be "operably joined" when they are covalently linked in such a way as to place the expression or transcription of the coding sequence under the influence or control of the regulatory sequences. In order for the coding sequences to be translated into a functional protein the coding sequences are operably joined to regulatory sequences. Two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region is operably joined to a coding sequence if the promoter region were capable of effecting transcription of that DNA sequence such that the resulting transcript might be translated into the desired protein or polypeptide.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium, or just a single time per host as the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells, which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove. However, the citation of any reference is not intended to be an admission that the reference is prior art.

EXAMPLES

Example 1

Determining the Level of Sialyl Transferase in the Mammary Gland

A reason for the incomplete sialylation of proteins produced in the mammary gland could be the limitation in the level of sialyl transferase in the mammary gland as compared to the level of sialyl transferase found in the liver, where serum proteins are normally secreted. To evaluate this hypothesis, the gene for 2,6 sialyl transferase was isolated from a cDNA library from goat liver. This cDNA was used as a probe in a Northern blot to determine the level of expression of the gene in the mammary gland vs. the liver. By Northern analysis, the level found of sialyl transferase expression in the mammary gland is about one percent of that found in the liver, implying a limitation in the sialylation capacity in the mammary gland.

Cloning of ST6 Gal1 from Goat Liver

A cDNA library was constructed using RNA isolated from goat liver. The known sequence of human ST6 was used to design PCR primers that could amplify the goat sequence. Following RT-PCR reactions, a full-length cDNA encoding 2,6 sialyl transferase, (ST6 Gal1), was isolated. The protein sequence of goat ST6 Gal1 is comparable to that of the human protein (See FIG. 1: GENE ID: 100861310 ST6GAL1, ST6 beta-galactosamide alpha-2,6-sialyltransferase-1 [Capra hircus]; FIG. 1 depicts both the goat (top: "Query"; SEQ ID NO:1) and human sequence of ST6 Gal1 (bottom: "Subject"; SEQ ID NO:2)

The gene encoding the 2,6 sialyl transferase was ligated into the goat beta casein expression vector to yield the plasmid BC2541 ST6Gal1 (See FIG. 2). This vector includes the goat beta-casein promoter to direct expression of linked genes into the mammary gland.

Generation of Transgenic Goats

The BC2541 ST6Gal1 transgene was used to generate transgenic goats that express the ST6Gal1 in their mammary gland. The resulting goats carry the beta-casein sialyl transferase gene in their genome. As shown below, the transgenic goats produce sialyl transferase in their milk.

Sialyl Transferase is Produced in the Mammary Gland ("In Vitro" Activity)

The presence of sialyl transferase in the mammary gland of the transgenic goats was confirmed using an assay to test for enzymatic activity of sialyl transferase. Namely, sialyl transferase can sialylate exposed 1,4 galactose on N-linked complex sugars.

Recombinant Alpha-1 antitrypsin, (AAT) when produced in the milk of transgenic goats is 50% sialylated, whereas AAT isolated from serum is almost completely sialylated (e.g., the commercially available Alfalastin®). The recombinant Alpha-1 antitrypsin produced in the milk of transgenic goats was used as a target for the sialylation reaction with sialyl transferase produced in the milk of transgenic goats. Milk from goats that express sialyl transferase in the mammary gland, along with nucleotide sugar CMP-sialic acid, was incubated with the undersialylated AAT. In addition, commercially available sialyl transferase was used as a control. The addition of sialic acid to the undersialylated AAT upon incubation was confirmed by running the incubated AAT on an isoelectric focusing gel (IEF gel). Increased levels of sialic acid on the protein (AAT) result in a lower isoelectronic point (pI) causing the protein to run lower on the gel. The recombinant AAT (which is 50% sialylated) is expected to run higher on the gel than the positive control, the fully sialylated AAT Alfalastin® isolated from serum.

Figure 3A:
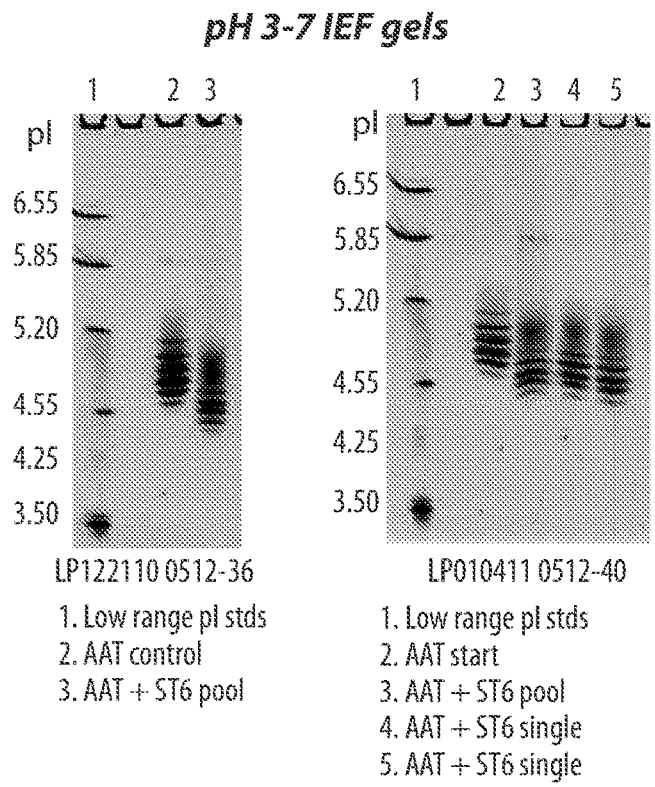
FIG. 3A depicts two gels: The gel in the left panel shows a pI standard ladder (lane 1), alpha-antitrypsin (AAT; lane 2), and AAT that was treated with a mix of commercially available sialyl transferases (lane 3). The gel in the right panel depicts a pI standard ladder (lane 1), AAT before treatment with a sialyl transferase (lane 2), AAT after treatment with a mix of commercially available sialyl transferases (lane 3), or AAT after treatment with a single sialyl transferase purified from the milk of a transgenic goat (lanes 4 and 5).

The left panel of FIG. 3A shows a sialylation experiment comparing AAT (lane 2) and undersialylated AAT that was treated with a mix of commercially available sialyl transferases (lane 3). As expected, the AAT that was subjected to sialyl transferases (lane 3) ran lower on the IEF gel than AAT that was not subjected to sialyl transferases (lane 2).

Similar results are depicted in the right panel of FIG. 3A. Treatment of undersialylated AAT with a sialyl transferase mix (lane 3) or purified batches of sialyl transferases from milk (lanes 4 and 5) resulted in increased levels of sialic acid compared and a downward shift compared to untreated undersialylated AAT (lane 2).

Figure 3B:
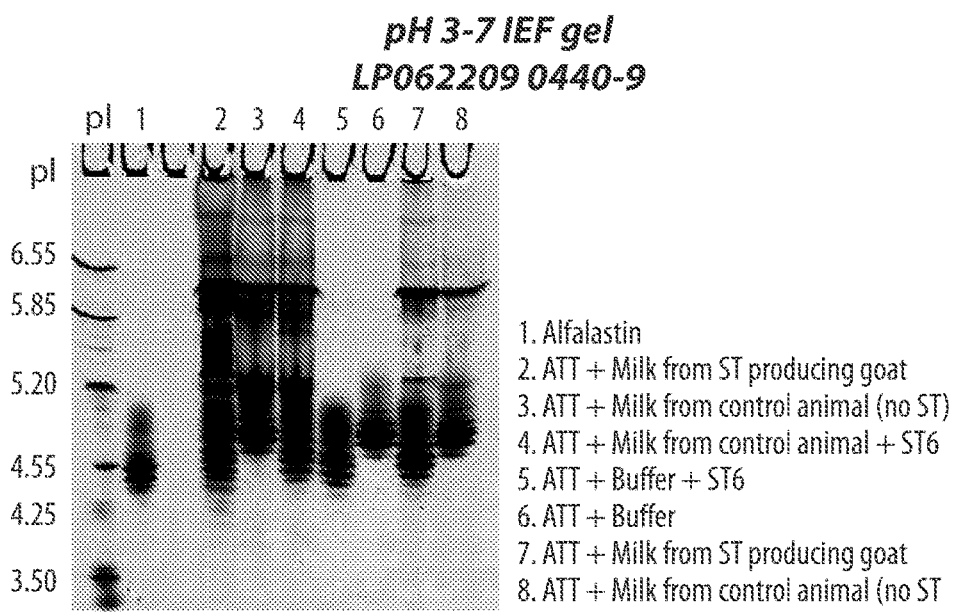
FIG. 3B depicts a gel showing Alfalastin®, a sialylated version of AAT (lane 1), AAT treated with milk from sialyl transferase producing transgenic goats (lane 2 and lane 7), AAT treated with milk from a control animal (lanes 3 and 8), AAT treated with milk from a control animal and transgenically produced sialyl transferase (lane 4), AAT treated with buffer and transgenically produced sialyl transferase (lane 5), and AAT treated with buffer (lane 6).

FIG. 3B depicts a gel showing Alfalastin®, a sialylated version of AAT (lane 1), AAT treated with milk from sialyl transferase producing transgenic goats (lane 2 and lane 7), AAT treated with milk from a control animal (lanes 3 and 8), AAT treated with milk from a control animal and transgenically produced sialyl transferase (lane 4), AAT treated with buffer and a transgenically produced sialyl transferase (lane 5), and AAT treated with buffer (lane 6).

Thus, as shown in FIG. 3, the sialyl transferase ST6Gal1 produced in the milk of transgenic goats is active "in vitro" and can sialylate undersialylated AAT to the level of plasma derived fully sialylated AAT.

Glycosylation Pattern of AAT Treated with Transgenically Produced Sialyl Transferase.

The transgenically produced sialyl transferase was purified from the milk of the transgenic animal and used to sialylate the target protein: undersialylated AAT. After subjecting the undersialylated AAT to sialyl transferase, the glycosylation of AAT was evaluated to confirm if sialic acid was added to the exposed Gal residues of the glycosylation side chains of AAT.

Figure 4:
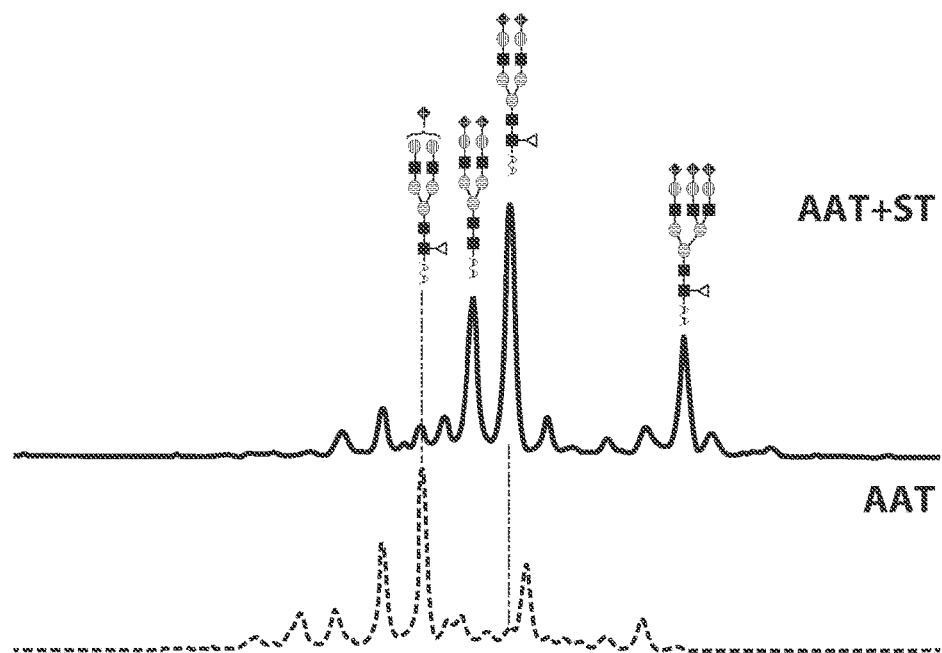
FIG. 4 provides a diagram showing the in vitro sialylation of alpha-1 antitrypsin with transgenically produced sialyl transferase.

As shown in FIG. 4, "in vitro" sialylation with sialyl transferase harvested from the milk of transgenic goats that produce sialyl transferase converts most of the mono-sialylated biantennary complex sugars on AAT to the bisialylated form. The lower graph shows AAT prior to sialylation while the upper graph shows AAT after being subjected to sialylation.

Sialyl Transferase Activity in the Mammary Gland ("In Vivo")

Sialyl transferase that is transgenically produced in the mammary gland was evaluated for its ability to increase the level of sialylation of recombinant proteins also being secreted by the mammary gland.

To test if the ST6Gal1 was active in the mammary gland, an endogenous protein was evaluated for the level of sialylation. Lactoferrin is an endogenous milk-produced protein that carries three N-linked glycosylation sites. Lactoferrin was isolated from the milk of a goat that carries the ST6Gal1 gene and produces sialyl transferase in its milk (FIG. 5, column 2). Lactoferrin was also isolated from control animal, which does not carry the ST6Gal1 gene (FIG. 5, column 1). The two lactoferrin samples, along with duplicate preparations, were treated with N-glycanase, derivatized with 2-aminobenzoic acid (2-AA), and the glycosylation pattern analyzed by HILIC LC-MS/(MS) with fluorescence detection. The results (FIG. 5) show that there is increased sialyl transferase activity in the transgenic mammal because the amount of bisialylated N-linked sugars on the lactoferrin is increased from 25% to 34% of the total sugar. The increase in bisialylation is correlated with the conversion of monosialylated sugars, which show a decrease from 18% in the control to 5% in the sialyl transferase expressing goat. Thus, the ST6Gal1 produced in the mammary gland converts most of the undersialylated monosialylated N-linked sugar to the bi-sialylated form. The ST6 Gal1 sialyl transferase, therefore, is active in the mammary gland and is capable of adding a sialic acid to a glycoprotein in the mammary gland.

Sialylation of Transgenically Produced Protein

Increasing expression of sialyl transferase in the mammary gland should result in an increase in sialylation of a recombinant protein also produced in the mammary gland. As shown above, ST6Gal1, when secreted into the milk, is active on AAT "in vitro". AAT was also used to evaluate the ability of transgenically expressed sialyl transferase to sialylate a transgenically expressed protein. Both ST6 Gal1 and AAT were co-expressed in the same mammary gland. This was achieved by crossing lines of goats carrying AAT with goats carrying the ST6 Gal1, resulting in mammals carrying both constructs. A male goat carrying the gene construct for expression of AAT into the milk (BC30) was crossed with a super-ovulated ST6Gal1 female. Embryos from this cross were isolated and implanted into foster mothers. From this procedure, 26 animals were born. Upon genetic testing, 2 females were identified that carried both the AAT and ST6 Gal1 gene constructs. In addition, 4 females carrying only the AAT construct were identified, providing a negative control.

Figure 6:
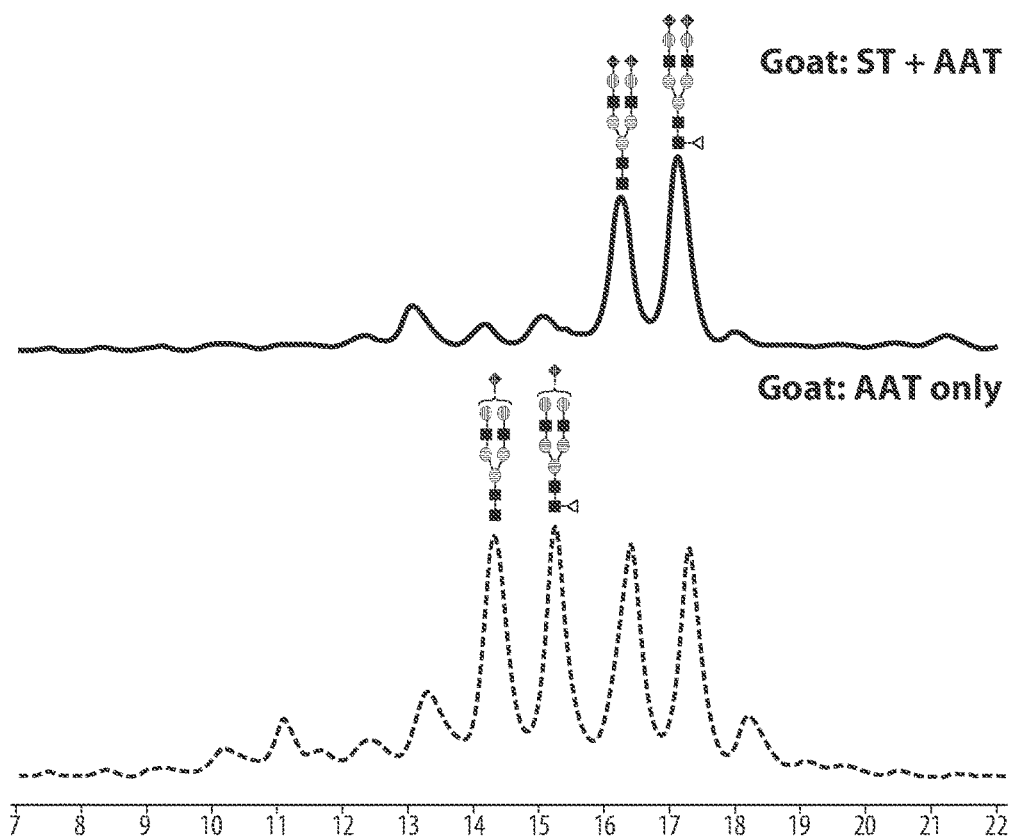
FIG. 6 shows the "in vivo" sialylation of AAT in the mammary gland of a goat producing both sialyl transferase and AAT (top graph) and AAT only (bottom graph).

At 3 months of age the animals that carry both the ST6Gal and AAT genes (and the control animals) were induced to lactate. The AAT was isolated from the animal carrying the ST6Gal1 as well as the control animals. The protein was analyzed with regard to the glycosylation, including the sialic acid content. As shown in FIG. 6, the bi-antennary N linked sugars on the control AAT animal are 50% bisialylated (bottom graph). However, the AAT isolated from the line carrying the ST6Gal1 construct was completely sialylated. The increased level of sialic acid on the AAT indicates the ability of the over expressed sialyl transferase to enhance sialylation of mammary gland expressed recombinant proteins.

Example 2

Determining the Level of 2,3 Sialyl Transferase In The Mammary Gland

The gene for 2,3 sialyl transferase is isolated from a cDNA library from goat liver. This cDNA library is used as a probe in a Northern blot to determine the level of expression of the gene in the mammary gland vs. the liver. A decrease in expression of the 2,3 sialyl transferase in the mammary gland compared to the liver could imply a limitation in the 2,3 sialylation capacity in the mammary gland.

Cloning of ST3 Gal1 from Goat Liver

A cDNA library is constructed using RNA isolated from goat liver. The sequence of human ST3 is used to design PCR primers that can amplify the goat sequence. Following RT-PCR reactions, a full-length cDNA encoding 2,3 sialyl transferase, (ST3 Gal1), is isolated. The gene encoding the 2,3 sialyl transferase is ligated into the goat beta casein expression vector to yield a plasmid, such as BC2541 ST3Gal1, including the goat beta-casein promoter to direct expression of linked genes in the mammary gland.

Generation of Transgenic Goats

An ST3Gal1-containing transgene is used to generate transgenic goats that express the ST3Gal1 in their mammary gland. The resulting goats carry the beta-casein sialyl transferase gene in their genome and produce sialyl transferase in their milk.

Production of Sialyl Transferase in the Mammary Gland ("In Vitro" Activity)

The presence of sialyl transferase in the mammary gland of the transgenic goats is determined using an assay to test for enzymatic activity of sialyl transferase. For example, sialyl transferase can sialylate exposed 1,4 galactose on N-linked complex sugars.

Recombinant Alpha-1 antitrypsin that is produced in the milk of transgenic goats is used as a target for the sialylation reaction with 2,3 sialyl transferase that is produced in the milk of transgenic goats. Milk from goats that express sialyl transferase in the mammary gland, along with nucleotide sugar CMP-sialic acid, is incubated with the undersialylated AAT. In addition, commercially available sialyl transferase is used as a control. The addition of sialic acid to the undersialylated AAT upon incubation is confirmed by running the incubated AAT on an isoelectric focusing gel (IEF gel). Increased levels of sialic acid on the protein (AAT) could result in a lower isoelectronic point (pI) causing the protein to run lower on the gel. The recombinant AAT (which is 50% sialylated) is expected to run higher on the gel than the positive control, the fully sialylated AAT Alfalastin® isolated from serum.

Glycosylation Pattern of AAT Treated with Transgenically Produced ST3.

The transgenically produced 2,3 sialyl transferase is purified from the milk of the transgenic animal and used to sialylate the undersialylated AAT. After subjecting the undersialylated AAT to sialyl transferase, the glycosylation of AAT is evaluated to confirm whether sialic acid has been added to the exposed Gal residues of the glycosylation side chains of AAT.

Sialyl Transferase Activity in the Mammary Gland ("In Vivo")

The 2,3 sialyl transferase that is transgenically produced in the mammary gland is evaluated for its ability to increase the level of sialylation of recombinant proteins also being secreted by the mammary gland or endogenous proteins secreted by the mammary gland (e.g., lactoferrin).

Sialylation of Transgenically Produced Protein

Increasing expression of sialyl transferase in the mammary gland could result in an increase in sialylation of a recombinant protein also produced in the mammary gland. AAT is used to evaluate the ability of transgenically expressed sialyl transferase to sialylate a transgenically expressed protein. Both ST3 Gal1 and AAT are co-expressed in the same mammary gland. This is achieved by crossing lines of goats carrying AAT with goats carrying the ST3 Gal1, resulting in mammals carrying both constructs. A male goat carrying the gene construct for expression of AAT into the milk (BC30) is crossed with a super-ovulated ST6Gal1 female. Embryos from this cross are isolated and implanted into foster mothers. Offspring are tested and those that carry both the AAT and ST3 Gal1 gene constructs are identified. Other offspring that carry only the AAT construct can be used as a negative control.

At 3 months of age the animals that carry both the ST3Gal and AAT genes (and the control animals) are induced to lactate. The AAT is isolated from the animals carrying the ST3Gal1 as well as the control animals, and the protein can be analyzed with regard to the glycosylation, including the sialic acid content.

Example 3

Pharmacokinetic Profiles

Figure 7:
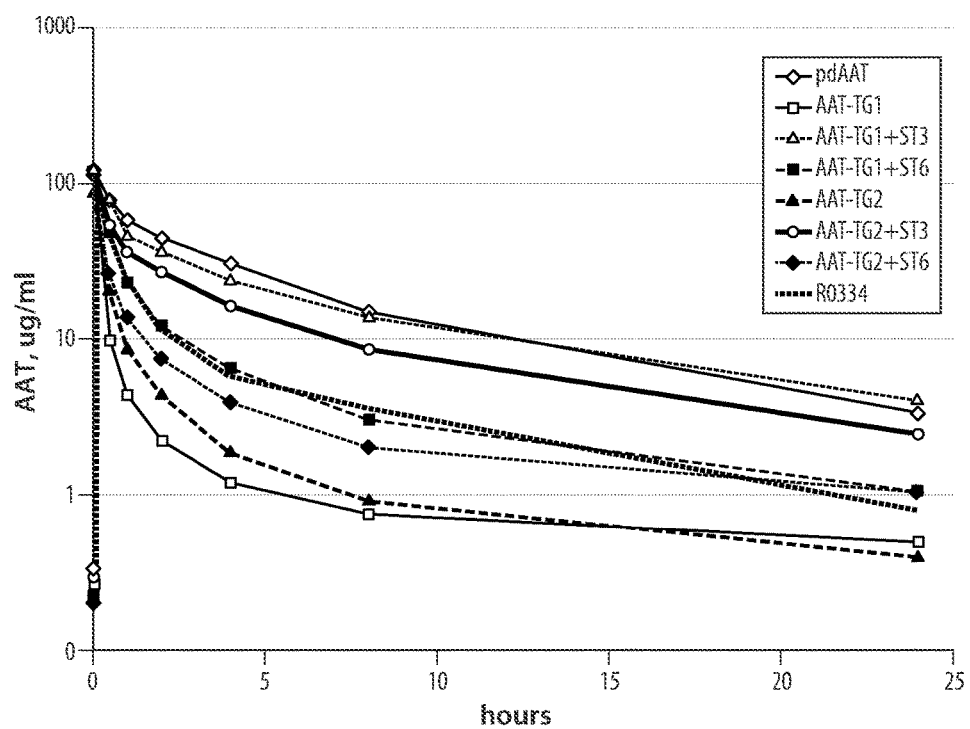
FIG. 7 shows the pharmacokinetic profiles of ST3 and ST6 sialylated transgenically produced-AAT compared to plasma-derived AAT (pdAAT).

Pharmacokinetic profiles of transgenically produced AAT that has been sialylated by ST3 or ST6 was compared to plasma-derived AAT (pdAAT) by analysis of the evolution of the concentration of AAT over a time period of 25 hours, as presented in FIG. 7.

FIG. 7 shows that AAT sialylated by ST3 or ST6 has a better half-life than no-sialylated AAT (pdAAT).

EQUIVALENTS

The foregoing written specification is considered to be sufficient to enable one skilled in the art to practice the invention. The present invention is not to be limited in scope by examples provided, since the examples are intended as an illustration of certain aspects and embodiments of the invention. Other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A method of producing a therapeutic protein with increased sialylation, the method comprising:
   providing a transgenic non-human mammal that has been modified to transgenically express a sialyl transferase and a therapeutic protein in mammary gland epithelial cells of the transgenic non-human mammal,
   wherein a gene encoding the sialyl transferase and a gene encoding the therapeutic protein are each integrated into the genome of the transgenic non-human mammal, and wherein the expression of the sialyl transferase and the therapeutic protein is under the control of at least one milk promoter;
   expressing the sialyltransferase and the therapeutic protein; and
   harvesting the therapeutic protein with increased sialylation from the mammary gland of the transgenic non-human mammal;
   wherein the sialylation of the therapeutic protein is increased by at least 10% compared to a therapeutic protein produced in a transgenic non-human mammal that has not been modified to transgenically express a sialyl transferase.

2. The method of claim 1, wherein the therapeutic protein with increased sialylation is a human protein.

3. The method of claim 1, wherein the protein with increased sialylation is an antibody.

4. The method of claim 1, wherein the protein with increased sialylation is antithrombin.

5. The method of claim 1, wherein the protein with increased sialylation is alpha-1 antitrypsin.

6. A transgenic non-human mammal that transgenically expresses a sialyl transferase and a therapeutic protein in mammary gland epithelial cells of the transgenic non-human mammal,
   wherein a gene encoding the sialyl transferase and a gene encoding the therapeutic protein are each integrated into the genome of the transgenic non-human mammal,
   wherein expression of the sialyl transferase and the therapeutic protein is under the control of at least one milk promoter, and
   wherein the sialylation of the therapeutic protein produced in the transgenic non-human mammal is increased at least 10% compared to a therapeutic protein produced in a transgenic non-human mammal that has not been modified to transgenically express the sialyl tranferase.

7. The transgenic non-human mammal of claim 6, wherein the therapeutic protein is a human protein.

8. The transgenic non-human mammal of claim 6, wherein the therapeutic protein is an antibody.

9. The transgenic non-human mammal of claim 6, wherein the therapeutic protein is antithrombin.

10. The transgenic non-human mammal of claim 6, wherein the therapeutic protein is alpha-1 antitrypsin.

11. The method of claim 1, wherein the transgenic mammal is an ungulate.

12. The method of claim 11, wherein the ungulate is a goat.

13. The method of claim 1, wherein the milk promoter is a goat beta casein promoter.

14. The method of claim 1, wherein the sialyl transferase is beta-galactosamide alpha-2,6-sialyltranferase and/or beta-galactosamide alpha-2,3-sialyltranferase.

\* \* \* \* \*